United States Patent
Kahn et al.

(10) Patent No.: US 10,231,687 B2
(45) Date of Patent: Mar. 19, 2019

(54) METHOD AND APPARATUS FOR ENHANCED X-RAY COMPUTING ARRAYS

(71) Applicant: Triple Ring Technologies, Inc., Newark, CA (US)

(72) Inventors: Paul Anthony Kahn, Los Gatos, CA (US); Christopher William Ellenor, Millbrae, CA (US); Tobias Funk, Martinez, CA (US); Oleg John Konings, San Francisco, CA (US)

(73) Assignee: Triple Ring Technologies, Inc., San Jose, CA (US)

( * ) Notice: Subject to any disclaimer, the term of this patent is extended or adjusted under 35 U.S.C. 154(b) by 320 days.

(21) Appl. No.: 14/885,166

(22) Filed: Oct. 16, 2015

(65) Prior Publication Data

US 2016/0106387 A1    Apr. 21, 2016

Related U.S. Application Data

(60) Provisional application No. 62/065,585, filed on Oct. 17, 2014.

(51) Int. Cl.
*A61B 6/00*    (2006.01)
*A61B 6/06*    (2006.01)

(52) U.S. Cl.
CPC .............. *A61B 6/5211* (2013.01); *A61B 6/06* (2013.01); *A61B 6/4028* (2013.01); *A61B 6/4071* (2013.01); *A61B 6/461* (2013.01)

(58) Field of Classification Search
CPC .................................................... A61B 6/5211
See application file for complete search history.

(56) References Cited

U.S. PATENT DOCUMENTS

| | | | | |
|---|---|---|---|---|
| 2010/0103804 A1* | 4/2010 | Koch | .................... | G06T 11/006 369/112.24 |
| 2013/0010920 A1* | 1/2013 | Wein | .................... | G06T 11/008 378/19 |

* cited by examiner

*Primary Examiner* — Dani Fox

(57) ABSTRACT

An x-ray imaging system utilizes enhanced computing arrays. A plurality of x-ray illumination source positions are utilized to produce x-ray radiation at each of the x-ray illumination source positions and to project x-ray radiation towards an object. A detector detects x-ray radiation from the object and transmits detector images for each of the illumination source positions. A memory buffer stores the detector images from the detector. A graphics processing unit formats the detector images and constructs a complete frame data set with the detector images for each of the illumination source positions. Another graphics processing unit receives the complete frame data set and performs image reconstruction on the complete frame data set.

20 Claims, 11 Drawing Sheets

| Table 1: Simulated contrast-to-noise ratio improvement for different iodine concentrations ||||| 
|---|---|---|---|---|
| Detector | 0.1 g/ml | 0.2 g/ml | 0.3 g/ml | 0.4 g/ml |
| integrating | 1 | 1 | 1 | 1 |
| Photon-counting | 1.10 | 1.10 | 1.09 | 1.09 |
| Energy resolving | 1.15 | 1.15 | 1.14 | 1.12 |

FIG. 9

METHOD AND APPARATUS FOR ENHANCED X-RAY COMPUTING ARRAYS

RELATED U.S. APPLICATION

This application claims priority to the U.S. provisional patent application Ser. No. 62/065,585, entitled "Method and Apparatus for Enhanced GPU Computing Device Arrays," with filing date Oct. 17, 2014 which is incorporated by reference herein in its entirety.

STATEMENT REGARDING FEDERALLY SPONSORED RESEARCH AND DEVELOPMENT

The U.S. Government may have a paid-up license in this invention and the right in limited circumstances to require the patent owner to license others on reasonable terms as provided for by the terms of Grant Nos. 5R44EB015910-03 awarded by the National Institute of Health (NIH).

FIELD OF THE INVENTION

The present invention relates to imaging and display systems. More particularly, the present invention pertains to a method and apparatus for enhanced computing device arrays in medical x-ray imaging and display.

BACKGROUND

X-ray imaging involving tomosynthesis or computed tomography can involve processing of large quantities of image data. The object is viewed from multiple angles and image data from each angle is processed and combined with tomosynthesis or computed tomography techniques. Imaging a moving object particularly a fast moving object such as a beating heart imposes further challenges on the imaging system. In order to present an image to the user with smooth or fluid motion, a frame rate of 7.5 or 15 or even 30 frames per second may be required, further increasing the amount of image data processed. When the x-ray imaging system is deployed in a surgical environment, e.g. cardiac catheterization, angioplasty or ablation, the image processing must be accomplished in real-time, introducing further performance and speed requirements to achieve processing in allowable time budgets.

A scanning electron beam x-ray imaging system can utilize an x-ray source array with multiple illumination focal spot positions e.g. hundreds or thousands of illumination focal spot positions. Each illumination focal spot position can generate a separate detector image and the performance and speed requirements imposed on the imaging system can be enormous particularly at high frame rates for real-time applications.

Graphics processing units (GPUs) can be utilized in high performance x-ray imaging systems. Use of GPUs can be beneficial over imaging systems based on central processing units (CPUs) because of the GPUs ability to process imaging data in parallel rather than the serial nature of CPUs. Performance of GPU-based x-ray imaging systems can be enhanced by using multiple GPUs. But when incoming imaging data is streamed to these GPU devices at a continuous rate, severe performance losses by the individual GPUs can occur. The performance losses can result in the use of additional GPUs in the imaging system increasing the cost and complexity of the system or can prevent the imaging system from achieving desired image quality and high frame rates.

What is needed is a cost-effective imaging and display system capable of processing and producing high quality images at high frame rates in a real-time environment. Furthermore, the imaging and display system should have speed and performance characteristics allowing use with multiple illumination focal spot positions and x-ray source arrays.

SUMMARY

The present invention pertains to a method and apparatus for x-ray imaging system utilizing enhanced computing arrays. A plurality of x-ray illumination source positions are utilized to produce x-ray radiation at each of the x-ray illumination source positions and to project x-ray radiation towards an object. A detector detects x-ray radiation from the object and transmits detector images for each of the illumination source positions. A memory buffer stores the detector images from the detector. A graphics processing unit formats the detector images and constructs a complete frame data set with the detector images for each of the illumination source positions. Another graphics processing unit receives the complete frame data set and performs image reconstruction on the complete frame data set. A scanning beam x-ray source can be utilized. A direct memory access unit can be utilized with one or more of the graphics processing units. A bus can be utilized to transfer the complete frame data set between graphics processing units in a single burst operation, which can be a PCI-E bus. Yet another graphics processing unit that receives a complete frame data set can be utilized to perform image reconstruction.

Detector images can be transferred from the detector at a rate of at least 1 MHz. The graphics processing units can utilize blocks of worker threads capable of performing independent calculations and memory operations. A complete frame data set can be produced at least once every 130 milliseconds. The complete frame data set can be transferred at a rate of 30 Hz. The complete frame data set can be transferred to one of the graphics processing units in a single burst operation. Detector images that are dropped from said complete frame data set can be identified. Image data for each of the illumination source positions can be aggregated to form the detector images. The first graphics processing unit can transpose the complete frame data set.

These and other objects and advantages of the various embodiments of the present invention will be recognized by those of ordinary skill in the art after reading the following detailed description of the embodiments that are illustrated in the various drawing figures.

BRIEF DESCRIPTION OF THE DRAWINGS

The present invention is illustrated by way of example, and not by way of limitation, in the figures of the accompanying drawings and in which like reference numerals refer to similar elements.

FIG. 9 is a table displaying contrast-to-noise improvement for different iodine concentrations for procedures in which iodine has been used as a contrast agent.

DETAILED DESCRIPTION

Reference will now be made in detail to embodiments of the present invention, examples of which are illustrated in the accompanying drawings. While the invention will be described in conjunction with these embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail as not to unnecessarily obscure aspects of the embodiments of the present invention.

Figure 1:
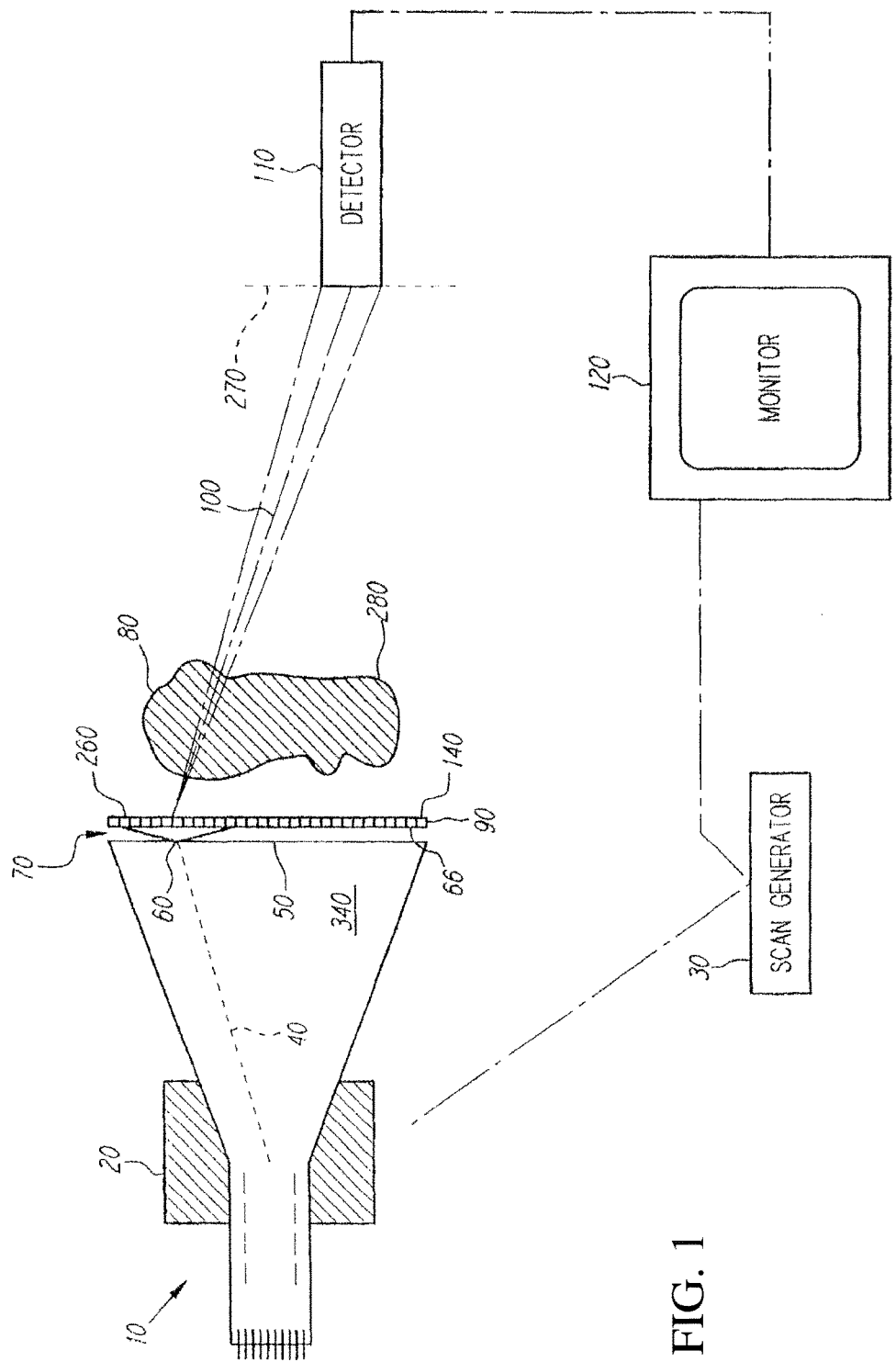
FIG. 1 is a diagram showing a portion of an exemplary scanning-beam x-ray imaging system of one embodiment of the present invention.

FIG. 1 is a diagram showing an exemplary imaging system of one embodiment of the present invention. The imaging system can comprise scanning x-ray source 10. X-ray source 10 can be the x-ray source described more fully in U.S. Pat. Nos. 5,682,412 and 6,198,802, entitled "X-Ray Source" and Scanning Beam X-Ray Source and Assembly" respectively, all of which are hereby incorporated herein by reference in their entirety. An imaging system is also further disclosed in U.S. Pat. Nos. 5,651,047, 6,183,139, 6,198,802 and 6,234,671, entitled "Maneuverable and Locateable Catheters," X-Ray Scanning Method and Apparatus," "Scanning Beam X-Ray Source and Assembly," "X-Ray System with Scanning Beam X-Ray Source Below Object Table," respectively, all of which are incorporated herein by reference in their entirety.

Use of scanning x-ray source 10 allows for utilization of a reverse geometry configuration for the imaging system. In a reverse geometry configuration, a smaller detector can be used whereas a point source requires a much larger detector. The area of the detector can be 2, 3, 4, 5, 6, 7, 8, 9, 10, 11, 12, 13, 14, 15, 16, 17, 18, 19 or 20 percent of the area of the maximum field of view for given source configuration and detector distance from patient or any percentage in between such percentages or any range of percentages in between such percentages. A smaller detector allows greater flexibility in positioning the detector with respect to the patient.

In a reverse geometry configuration, the detector can also be located further away from the patient than a detector with a point x-ray source. With a point x-ray source, the size of the detector required for a given maximum field of view size increases with the distance of the detector from the patient. The already large detector required with a point x-ray source becomes even larger with increasing distance. With a scanning x-ray source in a reverse geometry configuration, the size of the detector required for a given maximum field of view size decreases with the distance of the detector from the patient. Thus, the detector for scanning x-ray source 10 can be located with a distance from the patient of 1.3 m, 1.4 m, 1.5 m, 1.6 m 1.7 m, 1.8 m, 1.9 m, 2 m, 2.1 m 2.2 m, 2.3 m, 2.4 m, 2.5 m or any distance in between such distances or any range of distances in between such distances.

X-ray source 10 can comprise deflection yoke 20 under the control of scan generator 30. Deflection yoke 20 can comprise one or more magnetic focus or deflection coils. The magnetic focus or deflection coils can be made with insulated electrical wire wound around a core. The core can be ferrite, steel, iron or other magnetic alloy. An electron beam 40 generated within x-ray source 10 can be scanned across target 50 within x-ray source 10 in a predetermined pattern. Target 50 can be a grounded anode target. The predetermined pattern can be a raster scan pattern, a serpentine (or "S" shaped) pattern, a spiral pattern, a random pattern, a gaussian distribution pattern centered on a predetermined point of the target, or such other pattern as may be useful to the task at hand. The serpentine (or "S" shaped) pattern can eliminate the need in a raster scan pattern for horizontal "fly back."

As electron beam 40 strikes target 50 at focal spot 60, a cascade of x-rays 70 is emitted and travel outside of x-ray source 10 toward the object 80 to be imaged. To optimize system performance of the present embodiment, a cone of x-ray photons can be generated that will diverge in a manner that will just cover the multi-detector array 110. The detector including multi-detector array 110 is further described in U.S. Pat. No. 5,808,306, entitled "X-ray Detector," which is hereby incorporated herein by reference in its entirety.

This divergence can be accomplished by placing a collimating assembly between the target 50 of the scanning x-ray source 10 and the multi-detector array 110, and can be between the target 50 and the object to be imaged. The collimating assembly can be a collimation grid 90, comprising a grid of x-ray transmissive apertures 140. Collimation grid 90 can be designed to permit passage of only those x-ray pencil beams 100 whose axes lie in a path that directly intercepts multi-detector array 110. Collimation grid 90 can be stationary with respect to multi-detector array 110 while the system is in operation. Thus, as electron beam 40 is scanned across target 50, at any given moment there is only a single x-ray pencil beam 100 which passes through object 80 to multi-detector array 110.

The output of multi-detector array 110 can be processed and displayed on monitor 120 as luminance values. Image processing techniques can be used to produce a computer driven image on an appropriate display or photographic or other medium.

The imaging system disclosed herein is a low exposure system in that it can expose the patient at a rate of about 0.09 to 0.33 R/min with a 30 frame/sec refresh rate measured at the entrance to the patient, which in other systems under the same conditions can typically be between 2.0 to 2.8 R/min. Whole body exposure with a 30 frame/sec refresh rate can be lower as well.

Collimation grid 90 can comprise an array of apertures 140, the axes of each, are oriented or pointed toward multi-detector array 110. That is to say that the axes of apertures within the collimation grid 90 are not parallel to each other and form an acute to the line perpendicular to the output face 260 of the collimation grid 90. For example, a collimation grid for chest imaging can comprise apertures forming an angle with a line perpendicular to the output face 260 of the collimation grid 90 of between 0 degree at the center of the collimation grid 90 to as much as 20 degrees at the edge of the grid 90. A breast imaging application on the other hand can have a collimation grid 90 comprising apertures forming an angle with a line perpendicular to the output face 260 ranging to 45 degrees at the edge of the grid. Thus, a different collimation grid 90 can be selected and inserted for use in different imaging applications.

The number of apertures 140 in collimation grid 90 can correspond to the number of image pixels to be generated. For example, 500 by 500 to 1024 by 1024. Alternatively, the image pixel to aperture ratio can be increased, i.e., fewer apertures than image pixels may be used, in conjunction with the technique of "sub-sampling." The system spatial resolution can be determined, in part, by the pitch of the apertures in collimation grid 90. The precise number of apertures suggested above is illustrative only, and is not intended in any way to be limiting.

The x-ray absorbent portion of preferred collimation grid 90 can be designed to absorb errant x-rays so that they do not illuminate object 80. This can be accomplished by fabricating collimation grid 90 with sufficient thickness so that the x-ray radiation passing through an aperture 140 towards the multi-detector array 110 is substantially greater than the cumulative x-ray radiation passing through the x-ray absorbent portion in all directions other than toward multi-detector array 110. Such errant x-rays would provide the object 80 and attending staff with x-ray dosage but contribute no meaningful information to the image.

Square apertures 140 can be used and can be 0.0381 cm (0.015 in) by 0.0381 cm in dimension while round apertures can be 0.015 in (0.038 cm) in diameter. Both square and round apertures can yield a cross sectional area at multi-detector 110 that can be about $\frac{1}{100}$ the cross sectional area of other detectors. The cross sectional area of the face of the multi-detector array 110 can be much smaller than in other conventional systems. As a result, x-rays scattered at the object miss the multi-detector array and do not tend to fog the image as they do in other conventional systems which typically utilize relatively large surface area detectors.

Figure 2:
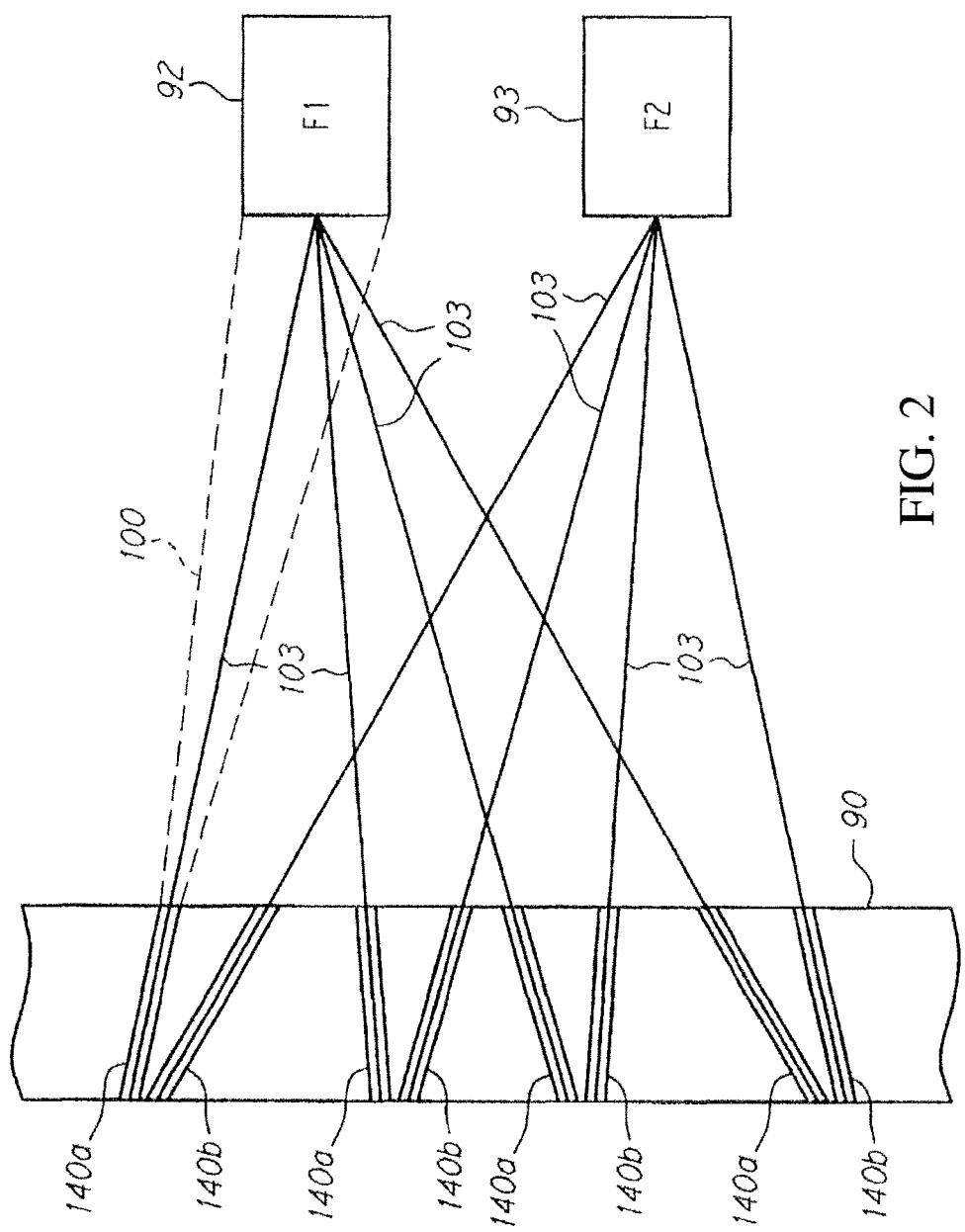
FIG. 2 is a diagram showing an exemplary scanning-beam x-ray imaging system of one embodiment of the present invention with a collimation grid having a plurality of focal points to obtain stereoscopic x-ray images.

FIG. 2 is a diagram showing an exemplary scanning-beam x-ray imaging system of one embodiment of the present invention with a collimation grid having a plurality of focal points to obtain stereoscopic x-ray images. The axes 103 of the x-ray pencil beams 100, corresponding to the aperture axes of every other row of apertures 140a in grid 90 can be pointed at focal point F1 at the center of multi-detector array 92 and the aperture axes of the remaining apertures are pointed at focal point F2 at the center of multi-detector array 93. One can scan the apertures in a raster or serpentine pattern and create a "line" of data from the first multi-detector array, and a line of data from the second multi-detector array. Repeating this, it is possible to build up two complete images, as seen from two distinct angles and thereby display them with conventional stereoscopic imaging display systems to provide a stereoscopic x-ray image.

Apertures 140a, 140b can diverge from a common first aperture 140 to form a "V" as shown providing separate paths along the "legs" of the "V" for x-ray pencil beams 100. There is no requirement, however, that apertures 140a, 140b diverge from a common aperture as shown, but an advantage of the "V"-shaped aperture where the x-rays enter at the common aperture or apex of the "V' is that both multi-detector arrays 92 and 93 can be illuminated simultaneously, the "V" acting as an x-ray splitter with some of the x-rays going to multi-detector array 92 and some to multi-detector array 93. This can decrease by 50% the power required for the beam current.

To achieve resolutions of several line pairs per millimeter or more at the object plane, the spatial resolution limit in some reverse-geometry systems is in large part determined by the size of the single non-segmented detector. Generally speaking, a small non-segmented detector can provide high spatial resolution while a large non-segmented detector provides high collection efficiency. This trade-off can be a problem in developing low dosage x-ray imaging systems.

When such a detector is small to increase resolution, a large proportion of the x-rays emitted by target 50 are unused by the single detector even when a collimator grid 90 is used. This is, in fact, how industrial reverse-geometry scanning-beam x-ray inspection systems are designed, where dose is usually not a consideration. Accordingly, while one can decrease the size of a detector by placing, for example, a lead washer in front of the single detector and thereby increase spatial resolution, the x-ray intensity and/or exposure time would have to be increased to maintain contrast resolution.

By fabricating a multi-detector array having a large area subdivided into multiple smaller detector array elements, a large capture area is achieved, while simultaneously through image reconstruction techniques retaining an image resolution that is comparable to the size of a single small detector element without increasing x-ray intensity and/or exposure time.

Figure 3:
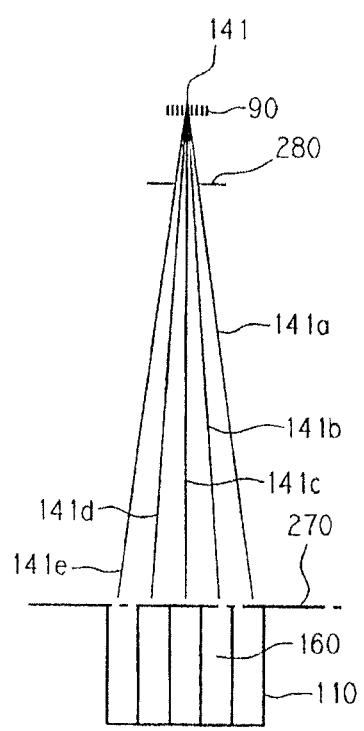
FIG. 3 is a diagram showing a single x-ray beam and generation of information for 5 image pixels.
Figure 4:
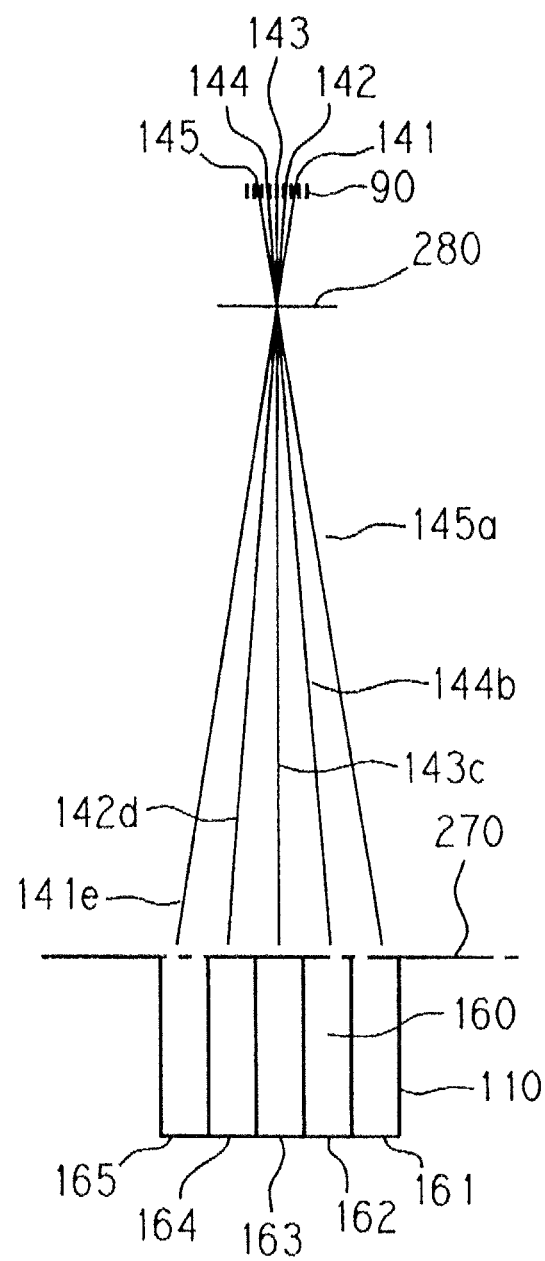
FIG. 4 is a diagram showing the sequential positions of the axes of x-ray micro-beams from x-ray pencil beams emanating from five consecutive apertures illuminating a single image pixel.

The resolution defined by the individual detector elements is maintained by distributing and summing the outputs from the individual detector elements into a memory buffer in which each address, i.e., image pixel, corresponds to a specific location in the object plane 280. As an electron beam 40 is moved discretely across the target 50, illuminating the area behind selected apertures 140 of the collimation grid 90, the address, to which the output of a given individual detector element is added, changes. The imaging geometry is shown in FIGS. 3 and 4. In FIG. 3, a single x-ray beam 100 is shown along with how it generates information for 5 image pixels. Effectively, the single x-ray pencil beam 100 emanating from individual aperture 141 is divided into x-ray micro-beams, the number of x-ray micro-beams created corresponding to the number of individual detector elements 160 which comprise the multi-detector array 110. In the case shown in FIG. 3, the axes of five x-ray micro-beams 141a, 141b, 141c, 141d and 141e are shown. In FIG. 4, the sequential positions of the axes of the x-ray micro-beams from x-ray pencil beams 100 emanating from five consecutive apertures 141 through 145 illuminating a single image pixel ("IP") are shown. The outputs from the individual detector elements 161, 162, 163, 164 and 165 receiving the x-ray flux from the five x-ray micro-beams, 145a, 144b, 143c, 142d and 141e respectfully, are added together to provide the luminance for the single pixel IP.

Stated differently, the output for each of the individual detector elements 160 is stored for later summation in an image buffer, at a memory address that corresponds to a very small specific region in the object plane 280, e.g., a single image pixel.

Accordingly, in one embodiment the memory storage address for the output of each individual detector element 160 changes with the position of the scanning x-ray beam 40 in an ordered fashion such that each memory address contains the sum of the radiation passing through a specific image pixel or spot in the object plane 280. In this way the spatial resolution of the system is determined by the size of a single individual detector element 160, while the contrast resolution of the system is determined by the area of all of the individual detector elements comprising the multi-detector array 110.

Figure 5:
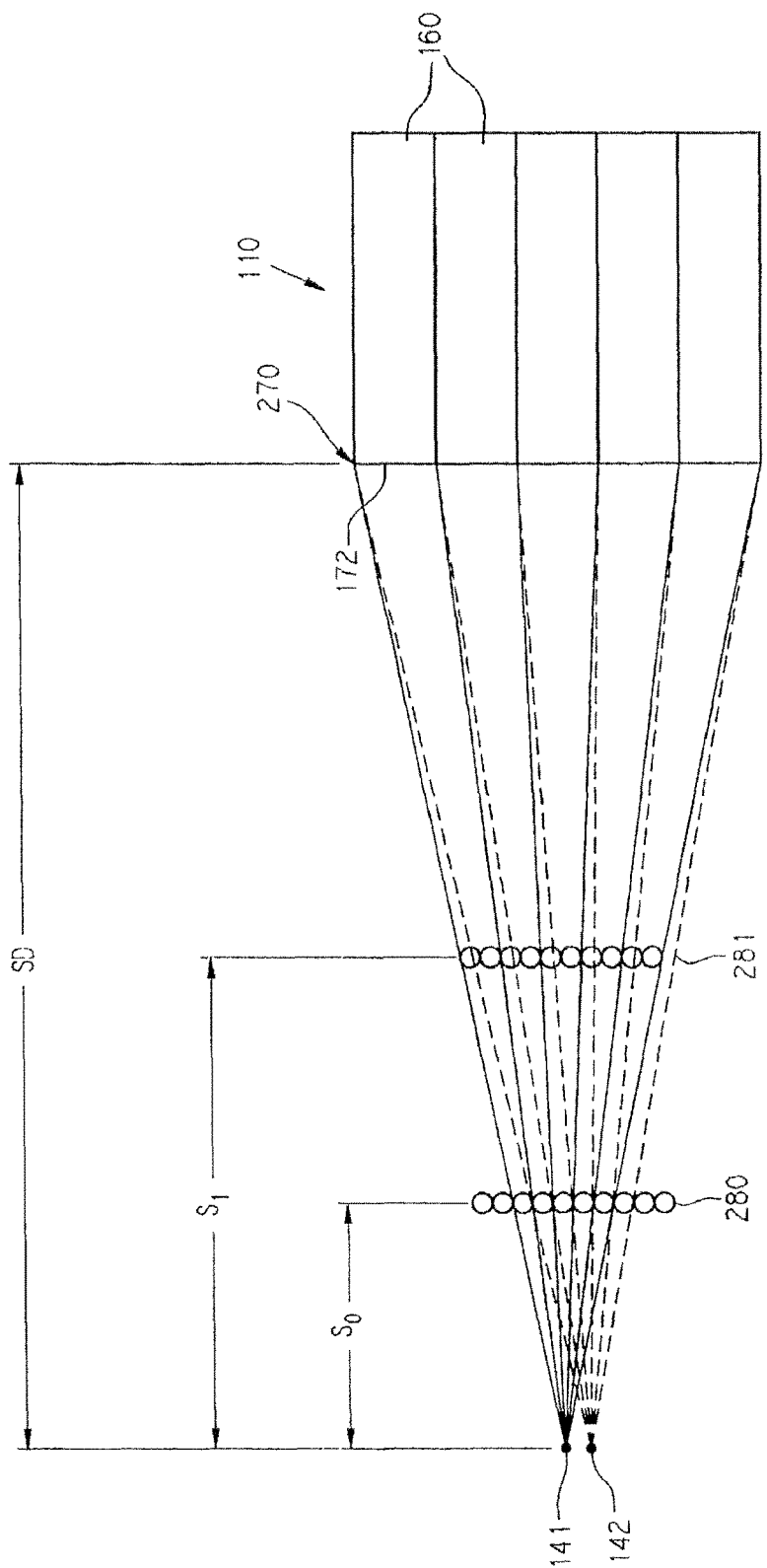
FIG. 5 is a diagram showing X-ray pencil beams from a first aperture and a second aperture passing through an object plane a distance $S_0$ from the apertures and passing through a plane a distance $S_1$ from the apertures.

An additional benefit of this multi-detector array imaging geometry is that the depth of field of the object plane 280 is narrowly defined. Structures lying in front of or behind it will be blurred (out of focus). X-ray pencil beams from a first aperture 141 and a second aperture 142 are depicted in FIG. 5 passing through an object plane 280 a distance $S_0$ from apertures 141,142 and passing through a plane 281 a distance $S_1$ from apertures 141, 142 where $S_1 > S_0$. The bubbles represent image pixels $IP_1$ through $IP_0$. As can be readily seen, the resolution at $S_1$ is less than that available at $S_0$. This feature provides for improved localization and visualization of detailed structures in the plane of interest 280, while providing an adequate depth of field that may be modified by the system geometry.

Conventional image intensifier technology typically has basic constraints that limit a system's sensitivity. A scanning-beam x-ray imaging system can result in the subject under examination being exposed to the lowest possible level of x-rays commensurate with achieving image quality adequate to meet the requirements of the procedure being performed. This means that the system used to detect the x-ray photons emerging from the subject preferably has the highest possible detective quantum efficiency. To achieve this, the scintillating material used in the individual detector elements preferably has a length in the direction in which the x-ray photons travel that is sufficient to ensure that no x-ray photons emerge from the end opposite the incident x-rays, i.e., the x-ray photon energy should be adequately dissipated in the material to maximize the output of the detector.

There are several types of individual detector elements which can be used in the scanning-beam x-ray imaging system. Semiconductor detectors using silicon, selenium, cadmium telluride, cadmium zinc telluride, or other materials can be used. Scintillators or optical detectors can also be used, for example, cesium iodide or cadmium tungstate scintillators with amorphous-silicon, CMOS, or CCD optical detectors. A scintillator in which x-ray photon energy is converted to visible light energy and the light intensity is then converted to an electrical signal by means of a photo-multiplier, photo diode, CCD or similar device can be utilized. Because the information from each aperture must be obtained in a very short time period, the scintillating material should have a fast response and a minimum afterglow time. Afterglow is the phenomenon wherein the scintillator continues to emit light after the stimulating incident x-rays have ceased. Even faster response and shorter afterglow times are required if x-ray intensity measurements are obtained using the x-ray photon counting technique.

One type of photon-counting detectors comprises detectors that convert incoming photons into charge carriers such as electrons or holes in a semiconductor material, or positive and negative ions in a gas or liquid material. An electric field applied to the material will sweep positive charges, such as positive ions or holes, towards one electrode and negative charges, such as negative ions or electrons, towards another electrode. As the charges accumulate on their respective electrodes, they form a current pulse. Such a current pulse can be analyzed using pulse-height analysis techniques to yield a count of the number of incoming photons.

With this type of photon counting detector, individual selected photons that strike the detector surface are counted by detecting a pulse of electrons or other charge carriers. The pulse of charge has significantly greater intensity than the charge detected between selected photons or when selected photons are absent.

A second type of photon-counting detectors comprises detectors that convert an incoming photon into several optical photons which together form an optical pulse. The optical photons can be in the visible range with wavelengths approximately within the range of from 400 nm to 700 nm; infrared photons with wavelengths longer than approximately 700 nm; or ultraviolet photons with wavelengths shorter than 400 nm. The optical pulse can be detected with an optical detector such as a CCD, a photo-diode, or a photo-transistor, thereby transducing the optical pulse into an electrical pulse. The electrical pulse can be analyzed using pulse-height analysis techniques to yield a count of the number of incoming photons.

The area of the circular active area of collimation grid 90 is preferably larger than the area of multi-detector array 110. Thus the axes of the x-ray pencil beams 100 emitted from the respective apertures 140 of collimation grid 90 all converge toward the multi-detector array 110 while each individual x-ray pencil beam 100 diverges, or spreads, as would a flashlight beam to cover the face of the multi-detector array 110.

Image reconstruction can be utilized to obtain high quality x-ray images. The output of the multi-detector array is preferably not applied directly to the luminance input of a video monitor. Instead, digitized intensity data for each image pixel are stored in a discrete address in a "frame store buffer". More than one such buffer may be used in certain applications. Pixel addresses within the buffer can be randomly accessed and the intensity value can be manipulated mathematically. This function has application in applying various image enhancement algorithms and it allows for pixel assignment of the data from discrete segments of the detector array.

Figure 6:
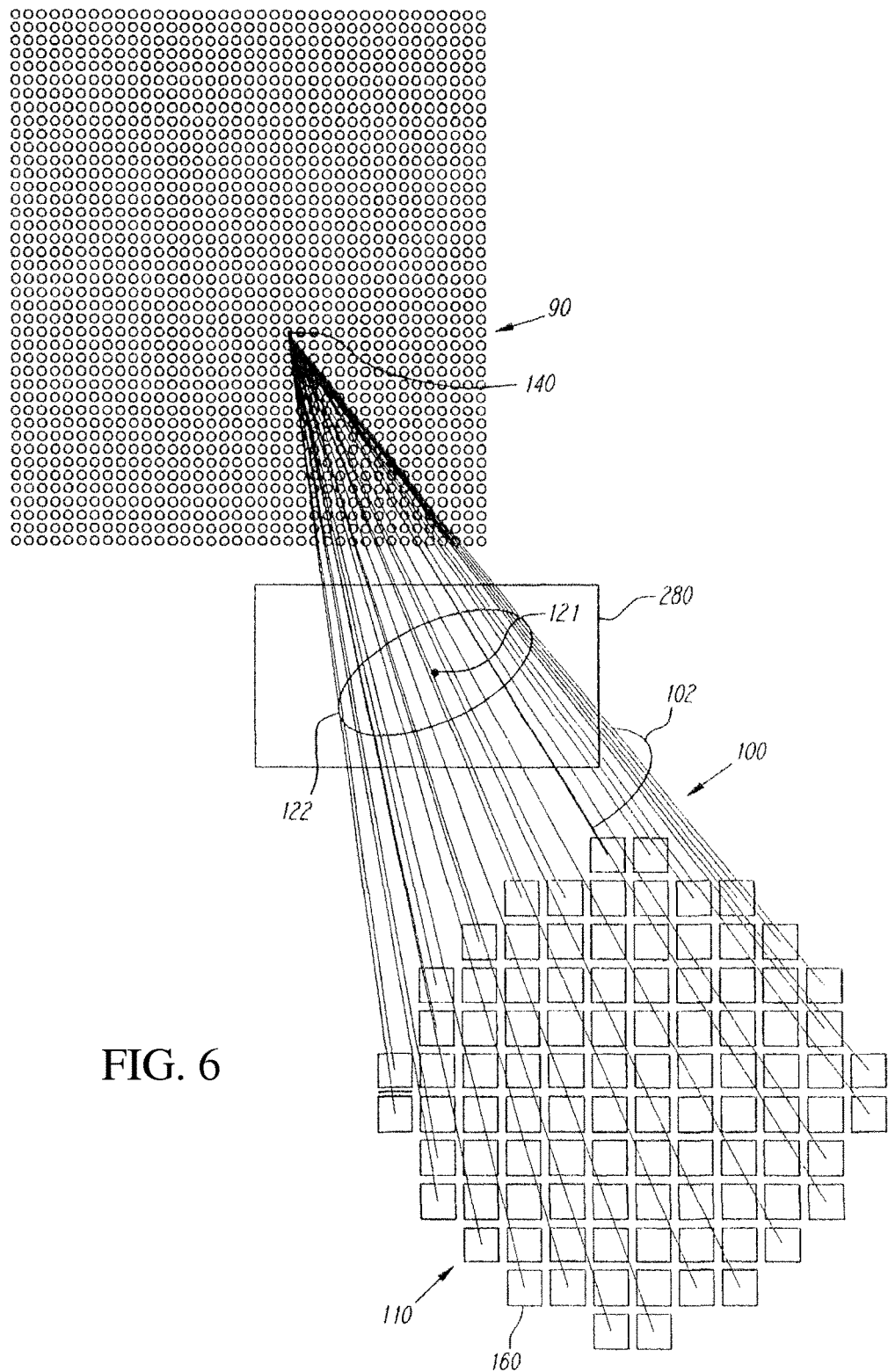
FIG. 6 is a diagram showing the divergence of a single x-ray pencil beam from an aperture to the multi-detector array and the intersection with an object at an object plane.

Referring to FIG. 6, this diagram illustrates the divergence of a single x-ray pencil beam 100 from aperture 140 to the multi-detector array and how it intersects an object 80 (not shown) at object plane 280. Image pixel 121 can be just one of the image pixels comprising the x-ray pencil beam intersection area 122 of object plane 280. A representative sample of the axes 102 of the x-ray micro-beams created by having a segmented array are also shown. In FIG. 6, x-ray pencil beam 100 is shown emitted through a single aperture 140 of collimator grid 90. X-ray pencil beam 100 as it exits aperture 140 can diverge forming a cone having a cross section the size of the aperture as it exits the aperture to a cross section covering the scintillators of the detector elements of the multi-detector array by the time it reaches 96 element multi-detector array 110. 96 element multi-detector array 110 can be positioned and designed such that the area of the cone of the x-ray beam 100 just covers the surface area of the multi-detector array 160 when the x-ray pencil beam 100 intersects the face of the multi-detector array.

As x-ray pencil beam 100 passes through object 80, information about object 80 can be detected by the multi-detector array 110 as x-ray intensity values. Because multi-detector array 110 is composed of 96 separate detector elements, each detector element 160 can detect only the intensity value for the particular x-ray micro-beam 101 of a segment of x-ray pencil beam 100 that it intersects with. The cross sectional shape and area of the x-ray micro-beams can correspond to the cross sectional area and shape as the input face of the detector elements. For example, if the input faces are square, the x-ray micro-beam can have a square cross section. The x-ray pencil beam 100 emitted from each aperture 140 on collimator grid 90 can therefore generate one group of 96 separate or discrete pieces of information (the intensity value at each detector element) about 96 areas of object 80 in the x-ray pencil beam's 100 path 122. The intensity information from each of the x-ray micro-beams can provide partial image pixel information which can be used to compile complete image pixel information for each image pixel in a desired plane of object 80.

Figure 7:
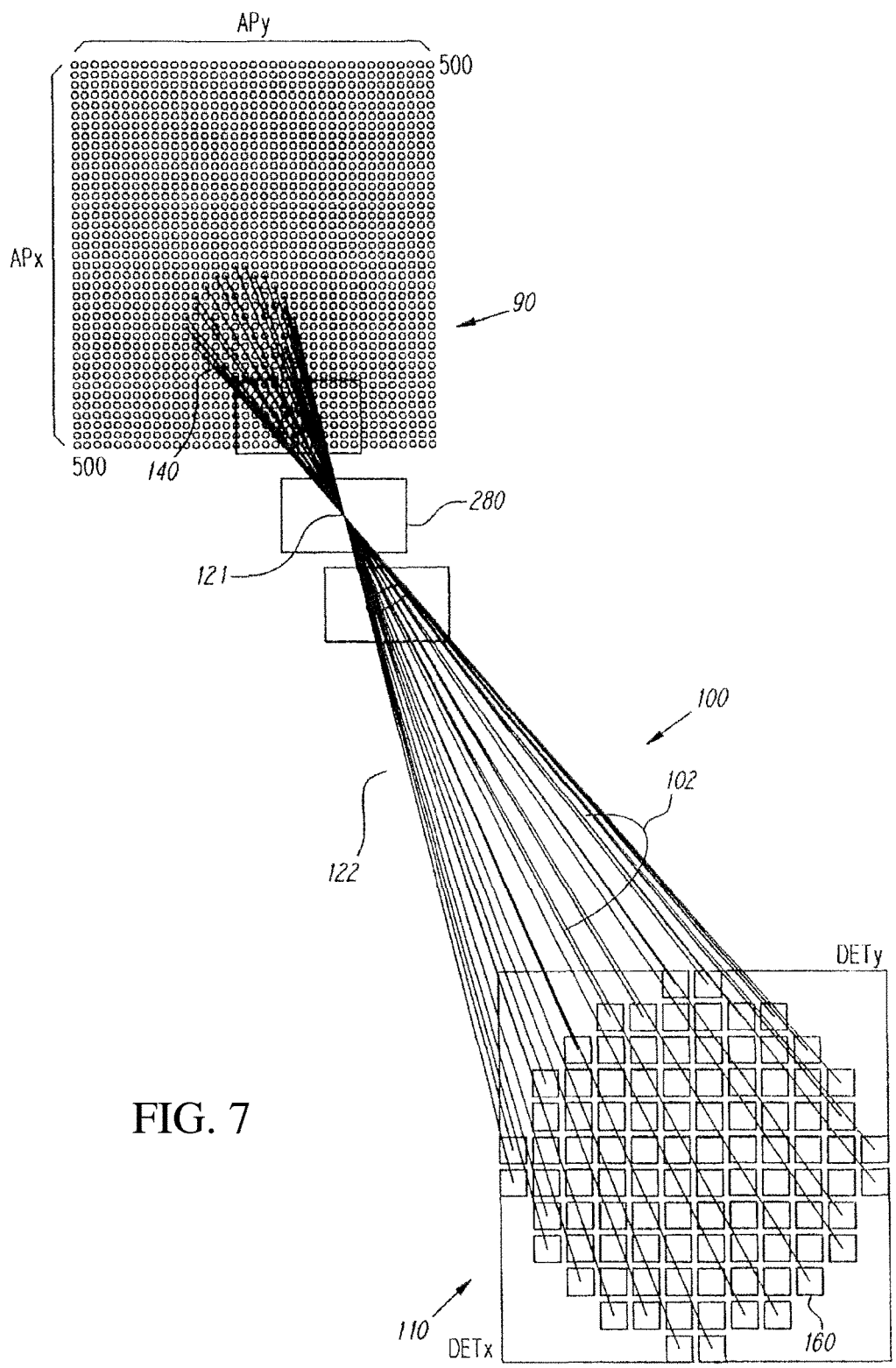
FIG. 7 is a diagram showing the axes of all of the x-ray micro-beams from all of the apertures that intersect a single image pixel in an object plane as they travel to the multi-detector array.

FIG. 7 illustrates the axes 102 of all of the x-ray micro-beams from all of the apertures 140 that intersect a single image pixel 121 in object plane 280 as they travel to the multi-detector array 110. This image pixel group of x-ray micro-beams can be ultimately processed to generate an image pixel on a video monitor. In one embodiment of the scanning-beam x-ray system, the apertures 140 on collimator grid 90 can generate x-ray pencil beams 100 in a predetermined pattern. As x-ray pencil beams 100 pass through an object, x-ray micro-beams 101 from adjacent and nearby apertures can intersect at, for example, point 121 (e.g. an image pixel) in the object. The intensity of each of these x-ray micro-beams 101 from these x-ray pencil beams 100 after they pass through the object can provide information about these intersecting points in the object. In this embodiment, each intersecting point on the object can therefore be considered a single-image "pixel" 121. In accordance with the techniques explained in more detail herein, each image pixel 121 can be mathematically reconstructed from the intensity information of the separate x-ray micro-beams 101 that were generated by the detector elements 160 for each of the emitted x-ray pencil beams 100 from, for example, the image pixel group of apertures that generated x-ray micro-beams whose axes passed through the object at that point, image pixel 121. In this example, a corresponding pattern of data assignment is repeated as the scanning x-ray beam passes behind all of the pixels.

In the displayed image, with a sub-sampling ratio of 1:1, the numerical value of each image pixel is equal to the sum of "n" parts where "n" is the number of detectors in the multi-detector array 110 (in this example, n=9). When constructed as shown in this example, the multi-detector array 110 together with the image reconstruction method selected, has the effect of fixing the working distance at which optimum focus is obtained and providing a plane of optimum focus.

The total area of the multi-detector array 110 should be large enough to intercept all of the x-rays in x-ray pencil beam 100 emanating from the collimation grid 90, to avoid exposing the patient to x-ray radiation which does not contribute to the image. Outside of the plane of optimum spatial resolution, SO (280 in FIG. 5 and FIG. 6), spatial resolution will degrade. In some applications, degraded spatial resolution outside of the depth of field of the system may be seen as being advantageous because blurring of detail outside of the area of interest may tend to increase the perception of details within the area of interest.

A number of methods can be used to obtain a usable image from the data obtained as described above. A simple convolution method may be used. Two additional methods can be utilized for obtaining maximal resolution and sensitivity from the captured data, the multi-image convolution method and the multi-output convolution method. An advantage of the multi-image convolution method over the multi-output convolution method is that the former allows the plane of optimum focus to be selected in software after the data is captured while the latter does not. The latter method, however, may be performed quicker where timing is a limitation.

The scanning-beam imaging system described herein can be used to generate a set of sequential planar images which can then be used to form a tomograph or a three dimensional display of the object 80. An image set can be analyzed to produce a three dimensional image consisting of a series of images at various depths by re-analyzing the data set with various values corresponding to planes of interest in the object 80.

An alternative image reconstruction method can be employed to reconstruct images along multiple focal planes. This image reconstruction method is referred to as m,n image reconstruction. It will be noted that there are numerous planes parallel to the source plane and detector plane where multiple beams pass through regularly-spaced points in the plane. These planes are referred to as focal planes or image planes. The regularly-spaced points are referred to as image pixels. Each focal or image plane comprise characteristics which differ from other focal planes, including distance from the source, spacing of image pixels, and size of the image plane. Due to partial image reconstruction around the perimeter of the image, the number of fully reconstructed image pixels is slightly lower than the above number and the total number of fully and partially reconstructed image pixels is slightly higher than the above number. The m,n image reconstruction method is more flexible than the previously described reconstruction methods. As described, m,n image reconstruction can generate a wide variety of focal planes at numerous positions between the source and detector planes. Many of the focal planes have a small pitch between image pixels which can be used to produce images with high spatial resolution. The ability to reconstruct a wide variety of focal planes can be used to move the focal plane with respect to the source and detector by simply selecting a suitable image plane near the region of interest of the object to be imaged. The m,n image reconstruction method can also be used to increase the effective depth of field of an image by simultaneously reconstructing multiple focal planes around a region of interest. The reconstructed planes can be combined to produce a single image with high spatial resolution over a larger range of distances from the x-ray source plane. The multiple reconstructed planes can be combined, for example, by adding together only the high spatial frequency components from each reconstructed plane.

Under one embodiment of the present invention, the imaging system utilizes the sub-sampling method to process the detected information. The sub-sampling method can be employed in a reverse geometry scanning beam x-ray system utilizing a sub-sampling ratio of 9:1 with a multi-detector array including ninety-six detector elements arranged in a pseudo-circle. The multi-image convolution method, the multi-output convolution method, m,n image reconstruction method and sub-sampling method is described more fully in U.S. Pat. No. 5,651,047 entitled "Maneuverable and Locateable Catheters" which has been incorporated herein by reference in its entirety.

To generate an image pixel, the processed x-ray intensity values detected by the multi-detector array 110 for each x-ray micro-beam passing through that image pixel IP are summed and output to a video monitor. For image reconstruction using a sub-sampling ratio of 1:1 each logical detector element of the logical array is capable of providing information about each image pixel in the object. For image reconstruction with a sub-sampling ratio of x:1, where x is a number greater than 1, less than all of the logical detector elements are capable of contributing information about a particular image pixel. The actual number capable of contributing information will depend on the particular sub-sampling ratio selected. With a sub-sampling ratio of 9:1, only 16 logical detector elements of the 144 logical detector element logical array will provide information about any particular image pixel.

In the sub-sampling method with a sub-sampling ratio of 9:1, the logical array can include sixteen virtual detectors. The virtual detectors can each include 9 logical detectors arranged in a 3 by 3 array. Alternatively, if a sub-sampling ratio of 4:1 were used, there would be 36 virtual detectors, each including 4 logical detector elements. Using a sub-sampling ratio of 1:1 there would be 144 virtual detectors each including 1 logical detector element.

Each of the 16 logical detector elements used to reconstruct a single image pixel using a sub-sampling ratio of 9:1 can be in different virtual detectors. Each virtual detector contributes partial image pixel information for nine different image pixels. Complete image pixel information is obtained by combining the information from the logical detectors in the same virtual array location from all 16 virtual detectors.

Additional image reconstruction methods and techniques can be utilized to generate information for a wide variety of planes and slices at numerous positions between the source and detector. These methods and techniques are described more fully in U.S. Pat. Nos. 6,178,223 and 6,181,764, entitled "Image Reconstruction Method and Apparatus" and "Image Reconstruction for Wide Depth of Field Images," all of which are hereby incorporated herein by reference in their entirety.

The images can be acquired, including reconstruction, and the exposure rates can be optimized using the methods described above and below, rapidly enough to create a continuous, real time video representation of the motion of the object, including organs such as one or more of the lungs, the heart, or other organs, or instruments, such as catheters or stents, or implantable objects such as valves, in real time.

The scanning-beam imaging system described herein can be used to generate a set of sequential planar images which can then be used to form a tomograph or a three dimensional display of the object 80. An image set can be analyzed to produce a three dimensional image consisting of a series of images at various depths by re-analyzing the data set with various values corresponding to planes of interest in the object 80.

Figure 8:
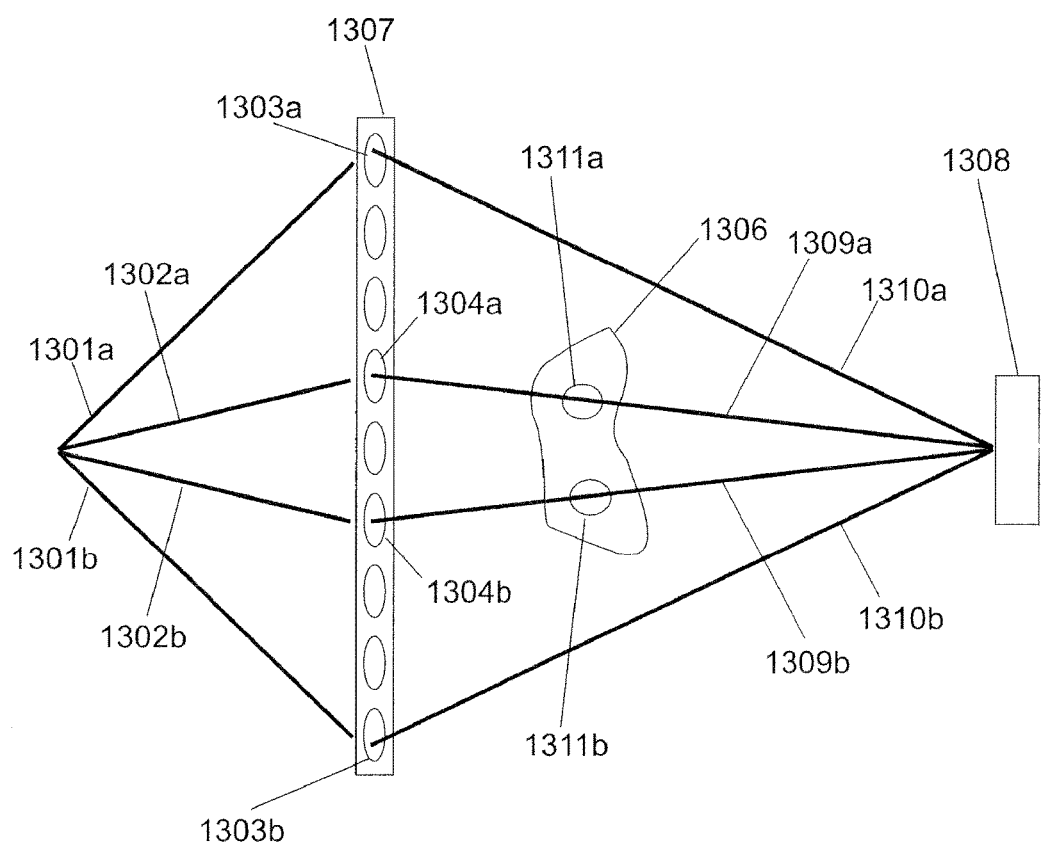
FIG. 8 is a diagram illustrating one embodiment of the present invention in which a region of interest has been defined within the patient volume.

FIG. 8 is a diagram illustrating one embodiment of the present invention. In FIG. 8 electron beams 1301a and 1301b impinge on focal points 1303a and 1303b of target 1307, and electron beams 1302a and 1302b impinge on focal points 1304a and 1304b of target 1307. Here, for simplicity, only one row of focal spots is shown, whereas in a preferred embodiment the target may be made of several rows of focal spots. When the electron beams 1302a and 1302b strikes target 1307 at focal spots 1304a and 1304b, x-ray beams 1309a and 1309b are created and measured by detector(s) 1308. An object, e.g. a human patient, to be imaged contains some region of interest 1306. Region of interest 1306 is shown here for simplicity as a single region, but in actuality could be 2, 3, 4, or more distinct regions of interest. In order to minimize the dose to the patient and reduce exposure to medical personnel, only the focal spots 1304a and 1304b and those between them are illuminated by the full electron beams 1302a and 1302b. As focal spots 1303a and 1303b would expose an area outside of region of interest 1306, patient dose is reduced by reducing electron beams 1301a and 1301b or redirecting the beams away from focal spots 1303a and 1303b. This process is referred to as region of interest filtering. It can be more specifically described as digital or electronic region of interest filtering, as the definition of at least one region of interest 1306 does not require the placement of mechanical components such as shutters, but instead is implemented by electronically controlling electron beams 1301a, 1301b, 1302a and 1302b.

In an embodiment of the present invention, detector 1308 is an energy resolving detector with two or more energy bins, preferably 10 or less bins, more preferably 5 or less bins, and most preferably 2 bins, and the contrast-to-noise ratio is optimized for a given contrast medium by weighting the number of detected x-rays in each bin by using the expression $$w(E) = \frac{1 - e^{-[\mu_c(E) - \mu_b(E)] \cdot d}}{1 + e^{-[\mu_c(E) - \mu_b(E)] \cdot d}}$$

as the weighting factor, wherein d is the thickness of the contrast medium, $\mu_c(E)$ is the energy dependent attenuation coefficient of the contrast medium, and $\mu_b(E)$ the attenuation coefficient of the background.

In another embodiment of the present invention, the exposure to x-rays of at least one person is optimized by modifying target 1307, and thereby modifying the shape of the x-ray energy spectrum, to best match the x-ray energy spectrum to one or more of: the needs of the procedure to be performed; the properties of the subject being imaged; the properties of the target organ to be imaged; any instrument that will be used during the procedure; and any contrast agents used during the procedure. The modification of target 1307 can involve the use of materials, wherein those materials are chosen from materials including but not limited to tungsten, copper, aluminum, beryllium, lead, rare earth elements including but not limited to gadolinium, and alloys or mixtures thereof.

It is an aspect of an embodiment of target 1307 that target 1307 comprises a tungsten layer in contact with the vacuum layer into which electron beam 1302a and 1302b impinges and creates x-rays 1309, and wherein the x-ray spectrum is modified by one or more layers of an additional material or materials. A modified target 1307 can comprise a beryllium sheet onto which a film of tungsten is deposited, while beryllium is in contact with a thin layer of cooling water, which is followed by thin aluminum sheet, and wherein the procedure may utilize iodine as a contrast agent, and wherein the procedure may be a cardiac intervention. FIG. 9 is a table displaying contrast-to-noise improvement for different iodine concentrations. In a further embodiment, there is at least one additional layer comprising at least one rare earth metal between the tungsten film and the beryllium sheet, where the at least one rare earth metal can comprise gadolinium.

There are many ways that region of interest 1306 can be defined. In a preferred embodiment, a healthcare provider is presented with an image (a recently acquired frame) from which to define region of interest 1306 or multiple regions of interest. The image from which the health care provider defines region of interest 1306 and other regions of interest that will be exposed to x-rays can be the entire field of view of the system, or any subset thereof, including a previously defined region of interest. The health care provider can define the region(s) of interest in many ways, but in a preferred embodiment the region(s) of interest(s) are defined by the health care provider drawing the region on a display device, preferably using a dedicated stylus but in other embodiments using a finger or any other object.

In another embodiment of the present invention, the control and imaging portions of the apparatus are used to automatically define a region of interest that is optimal for the procedure to be performed, using methods chosen from a list including but not limited to: identifying an organ of interest, identifying a tumor, utilizing image data taken previously of the patient, using an algorithm that uses patient data including but not limited to height, weight, body mass index, age, sex, race, medical status or conditions, chest size, and/or length of arms or legs.

To further reduce the x-ray dose delivered to the patient as well as reduce the exposure to x-rays of health care providers, one embodiment of the present invention determines the minimum amount of x-ray radiation required to make a reconstructed image with a sufficient signal-to-noise ratio and resolution for the procedure to be performed, in at least one region of the object, preferably in more than one region, e.g. in region 1311a and region 1311b. Further, the apparatus then limits the x-ray dose to regions 1311a or 1311b to that minimum required amount. This is referred to herein as equalization filtering.

As shown in FIG. 8, there are two separate regions 1311a and 1311b to which equalization filtering may be applied. To apply equalization filtration, the x-ray absorbance of regions 1311a and 1311b are determined by exciting focal spots 1304a and 1304b with electron beams of known qualities. This causes the formation of x-ray beams 1309a and 1309b which pass through regions 1311a and 1311b and are subsequently detected by detector 1308. Based on this measurement, electron beams 1302a and 1302b are modified in a way that reduces the total x-ray dose to regions 1311a and 1311b to only that needed to achieve the signal-to-noise ratio required at the image resolution necessary to complete procedure being performed. The adjustable properties of electron beams 1302a and 1302b may be chosen from a list including but not limited to voltage, current, or duration. In a preferred embodiment the electron beams are raster-scanned over the focal spots on target 1307, dwelling on each targeted focal spot for a predetermined amount of time. The reconstructed image is formed from 2 or more raster scans of the electron beams over target 1307, and the equalization filtration is implemented by adjusting the number of times the electron beams dwell on each focal spot 1304a and 1304b. This method is herein referred to as digital equalization filtration.

In one embodiment of the present invention, the dose of x-rays to a patient is minimized by determining the amount of x-ray radiation detected by one or more pixels in one or more detectors, e.g. detector 1308, during an image acquisition and terminating the delivery of radiation to a region of the patient, e.g. region 1311a or 1311b, based on a threshold amount of measured x-ray radiation detected by the one or more detectors or detector pixels. In the digital equalization filtration method described above, this is implemented by measuring the amount of x-rays being detected by at least one detector or at least one pixel in at least one detector and during dwells of electron beam 1302a and 1302b on a focal spot 1304a and 1304b; determining a sum total of x-rays detected during one or more dwells of electron beam 1302a and 1304b on a focal spot 1304a and 1304b; and skipping future dwells to be performed on that focal spot 1304a and 1304b during that image acquisition when the sum total exceeds a predetermined threshold amount. This process is repeated for each focal spot 1304a and 1304b to be used. This embodiment has the advantage of a high signal-to-noise ratio for the determination of whether the signal measured has exceeded the threshold value.

In another embodiment of the present invention, the amount of x-rays detected during the first dwell of x-ray beam 1302a and 1304b on each focal point 1304a and 1304b is used to then compute the expected number of dwells required to measure a sufficient amount of x-rays to create an image of the required signal-to-noise and resolution, and that number of dwells is used during the imaging process. This determination is repeated for each focal spot to be used. This method has the advantage of being less computationally intensive but suffers from lower signal-to-noise than the previous embodiment.

Due to software or hardware limitations, it may be preferable to limit the number of changes in the number of dwells between subsequent focal spots during the raster scan of target 1307. This can be achieved by an algorithm that allows a range of values for the threshold value, for example by putting in some hysteresis that stops the number of dwells from bouncing up and down due to noise, for example Poisson or "shot" noise, in the number of x-rays arriving during the dwells during the raster scan.

It is preferable to perform equalization filtration in real time, i.e. during each image acquisition, by adjusting the exposure time or some other property of the electron beam to optimize the number of x-rays emitted from each focal spot as the imaging system runs. This has the advantage of not only minimizing the x-ray dose to the patient but also providing an optimized reconstructed image for each acquisition, for example each frame in a video image, by removing artifacts and issues due to, for example, heart rate and/or respiratory rate. However, the previously discussed embodiment of the present invention that minimizes the dose of x-rays to a patient by determining the amount of x-ray radiation detected by one or more detectors or pixels in one or more pixelated detectors during an initial image acquisition, and based on that measurement, delivering an optimal, reduced, amount of x-ray radiation to a region, e.g. region 1311a or 1311b, of the patient during one or more subsequent image acquisitions has the advantage of being less computationally intensive.

Other data and methods can be used to implement and refine equalization filtration, using methods chosen from a list including but not limited to: identifying an organ of interest, identifying a tumor, utilizing image data taken previously of the patient, using an algorithm that uses a predefined model of a region to be imaged and optionally includes patient data including but not limited to height, weight, body mass index, body fat percentage, age, sex, race, medical status or conditions, and/or size of a body region to be imaged, including but not limited to thickness, length, height, volume, and/or circumference, including but not limited to the size of the subjects chest, abdomen, waist, neck, head, arms, or legs, and using this information to modify the amount of radiation delivered to the various regions to be imaged. These techniques are preferably combined with the digital equalization filtration embodiments described above and/or combined with the electronic region of interest filtering described above.

In one embodiment of the present invention, image equalization is implemented using information about a reconstructed image, said image being a previously acquired image, e.g. an earlier frame. In this embodiment, it is preferable that the previous image be a recently acquired image, ideally in the range of 1 to 20 images previously acquired, and may be chosen from 1, 2, 3, 4, 5, 10, 15, or 20 images previous. It may be advantageous to utilize only image data from a subset, or region, within the final reconstructed image.

In another embodiment of the present invention, equalization filtration is implemented using a preliminary, interim reconstruction generated by x-rays detected from one or more detectors or one or more pixels in one or more detectors during a subset of the final dwell time on one or more focal spots. It is preferable that the subset of the final dwell time includes the first dwell and may optionally include data from the first and second; first, second, and third; first, second, third, or fourth; or any other combinations of the available dwells, including but not limited to during the first 3, 4, 5, 6, 7, 8, 9, 10, 11, 12, 13, 14, 15, 16, 17, 18, 19, or 20 dwells, or during the first ¼, ⅓, ½, ⅔, or ¾ of the maximum number of dwells.

For digital equalization filtration, it is preferred that every time the electron beam dwells on focal spot 1304a or 1304b, the length of time it dwells on focal spot 1304a or 1304b is characterized by a predefined dwell time chosen from zero milliseconds (if region of interest filtering is simultaneously used and has determined that focal spot 1304a or 1304b does not illuminate the region(s) of interest) to a predetermined non-zero dwell duration. The total dwell time for focal spot 1304a or 1304b may then be the predetermined non-zero amount of time multiplied by the number of non-zero dwell time dwells for focal spot 1304a or 1304b, and the dwell time for other focal spots may be similarly determined. The amount of delivered x-ray radiation can be adjusted by adjusting the number of non-zero duration dwells. The properties of the electron beam including but not limited to voltage, current, focusing, or dwell time per dwell can be the same for all focal spots used in target 1307, but these may also be adjusted to implement or refine equalization filtration.

For the digital equalization filtering described herein, it is preferred to reconstruct each image based on both the amount of x-ray radiation detected by the at least one pixel of the at least one detector 1308, and the number of non-zero dwell time dwells for each corresponding focal spot 1304a and 1304b. In an embodiment of the present invention, the amount of radiation detected by the at least one detector 1308 summed over the total number of dwells per image is divided by the number of dwells or the total dwell time of the electron beam 1302a or 1302b on the corresponding focal spot 1304a or 1304b and this normalized detected x-rays per dwell or per unit time is used in subsequent image reconstruction.

X-ray detector 1308 can include any usable technology, and may be chosen from a list including but not limited to: a photon counting detector, a charge-integrating detector, or an energy resolving detector.

In an embodiment of the present invention, detector 1308 is a photon counting detector, and the dwell time and/or the number of fixed dwells is modified by truncating the exposure of focal spot 1304a and 1304b to electron beam 1302a and 1304b when the number of photons detected by detector 1308 exceeds a pre-determined threshold number, and similarly truncated for other focal spots.

In an embodiment of the present invention, detector 1308 and/or other detectors are photon counting detectors or more preferably energy resolving detectors, and the dwell time and/or the number of fixed dwells is modified by truncating the exposure of focal spot 1304a and 1304b to electron beam 1302a and 1304b when the number of photons detected by detector(s) 1308 exceeds a pre-determined threshold number wherein the threshold number is modified based on one or both of: the number of photons detected in at least one energy bin by at least one pixel or detector 1308 during a previously dwelled upon different focal spot or focal spots; or the number of dwells before the threshold was reached during exposure of a previously dwelled upon different focal spot or focal spots during a given raster scan. This has the advantage that the threshold can be modified to minimize the number of changes in the number of dwells between subsequent focal spots in the scan of target 1307, simplifying the mechanism and the method, and/or allowing it to run faster.

Under an alternative embodiment of the present invention, x-ray dosage and radiation on object 80 or the patient and attending staff can be further reduced by use of adaptive methods and apparatus. The imaging system may or may not be used in conjunction with a radiation source and may or may not be part of a radiation therapy system. X-ray imaging of the human body involves x-rays penetrating through different regions with highly varying attenuations; the intensity of x-rays reaching a detector depends on the amount the x-rays from a source were scattered and absorbed within the patient volume. Areas of the x-ray image can be overexposed with the result that object 80, the patient and attending staff can be exposed to unnecessary dose or x-ray radiation.

The adaptive methods and apparatus of one embodiment of the present invention can reduce x-ray dose and radiation and can be utilized for real-time x-ray imaging. Rather than acquiring the full-field image with a single exposure, the imaging system can use many exposures or projections of small areas of object 80 to generate the image, the number of exposures or projections can be as high as thousands. For a 7-inch field of view, up to 9,000 exposures or projections can be used. Multiple exposures or projections are possible through use of a scanning-beam x-ray source or a multi-pixel carbon nanotube x-ray source or discrete cathode x-ray source or other multi-pixel x-ray sources as source 10. Each exposure or projection can significantly overlap with neighboring exposures or projections, thus the exposures or projections can be redundant. Rather than using the same exposure for every projection, the imaging system exposes every projection with just sufficient exposure to obtain the desired image quality. For example, lungs may be a body part requiring less exposure to obtain an image of a given quality, as their attenuation characteristics permit the penetration of a relatively large percentage of incident x-ray radiation. Therefore, in an embodiment of the present invention utilizing a scanning-beam x-ray source or a multi-pixel carbon nanotube x-ray source or discrete cathode x-ray source or other multi-pixel x-ray sources, the imaging system may expose the lung to less radiation than other body parts that are relatively x-ray opaque, such as the heart, and still achieve sufficient image quality. The imaging system can adjust exposures and radiation by using different tube voltages, beam currents, exposure times, repetitions of fixed-length exposures, or the combination of the former. One setting can be 120 kV tube voltage at 17 kW power and another setting can be 80 kV tube voltage at 9 kW power. Reducing the exposure or radiation is not the only benefit. The imaging system also can define preselected regions of interest for increased image quality and other regions with lower image quality. Thus, regions of interest that require high image quality, can receive more exposure through increased repetition of fixed-length exposures of that region, different tube voltages, beam currents, exposure times, or the combination of the former.

Under an alternative embodiment of the present invention, source 10 can be a scanning-beam X-ray source. Electron beam 40 can be swept across X-ray target 50 and dwells at distinct focal spot 60 positions for a predetermined exposure time, which depends on the frame rate and the size of field of view. At a frame rate of 15 fps (7" mode field of view), the exposure time is 8 μsec. This exposure time is broken into 1 μsec illuminations (rescans) separated in time. For given material selection and dimensions of x-ray target 50, use of 1 μsec illuminations can keep the temperature of x-ray target 50 below desired maximums (maximums being set by the potential of the target to "burn out" when overheated by the incident beam in a localized region). Thus, every focal-spot position is rescanned several times. Different size or aspect ratio of field of view can also be used, 5"×5", 5"×10", etc, or, 6", 7", 8", 9", 10", 11", 12", 13", 14" or 15".

The imaging system can utilize equalization or region of interest filtration or both. For both equalization or region of interest filtration, offline implementation or real-time implementation can be utilized. The imaging system can acquire images from up to 9,000 different focal-spot positions for each full-field image. Each acquisition can be repeated up to 8 times (8 rescans). With 7" field of view, this results in a frame rate of 15 fps. Alternatively, each acquisition can be repeated 2, 3, 4, 5, 6, 7, 9, 10, 11, 12, 13, 14, 15, 16, 17, 18, 19 or 20 times (rescans). The imaging system can aggregate the rescans or it can save each rescan separately (rescan images). Each rescan can be saved as a separate file and can be buffered. Alternatively, the rescans can be aggregated immediately.

Under an alternative embodiment of the present invention, the imaging system can implement equalization filtration using separate or aggregated rescan images. In this embodiment, the imaging system may first determine a target number of photons per detector image. It may then determine the number of photons in the rescan image(s) and aggregate rescan images until at least the target number of photons is reached or all 8 rescans are added. This procedure yields a "rescan map" detailing how many rescans are needed per focal spot position and a modified detector image file that can be reconstructed with the reconstruction engine.

Equalization filtration not only saves dose but can be a very effective way to compress dynamic range and thereby improve image quality. As previously discussed, equalization filtration can dynamically and automatically vary the exposure depending on the opacity of the region exposed. Hence, it can compress the dynamic range by reducing exposure significantly in translucent areas such as the lung field and maintain exposure in more opaque regions.

Under another embodiment equalization is performed by variation of the beam current and the beam current is adjusted according to the flux measured at the detector. Importantly the beam current can start at low values to not saturate the detector even with no attenuator, e.g. no patient, present. With an attenuator present this low beam current will result in a very low flux being detected at the detector. Feedback relaying detected flux can lead to up-regulation, i.e. increasing, of the beam current until desired flux is achieved. The up-regulation can be done during a single exposure or implemented via rescans.

Figure 10:
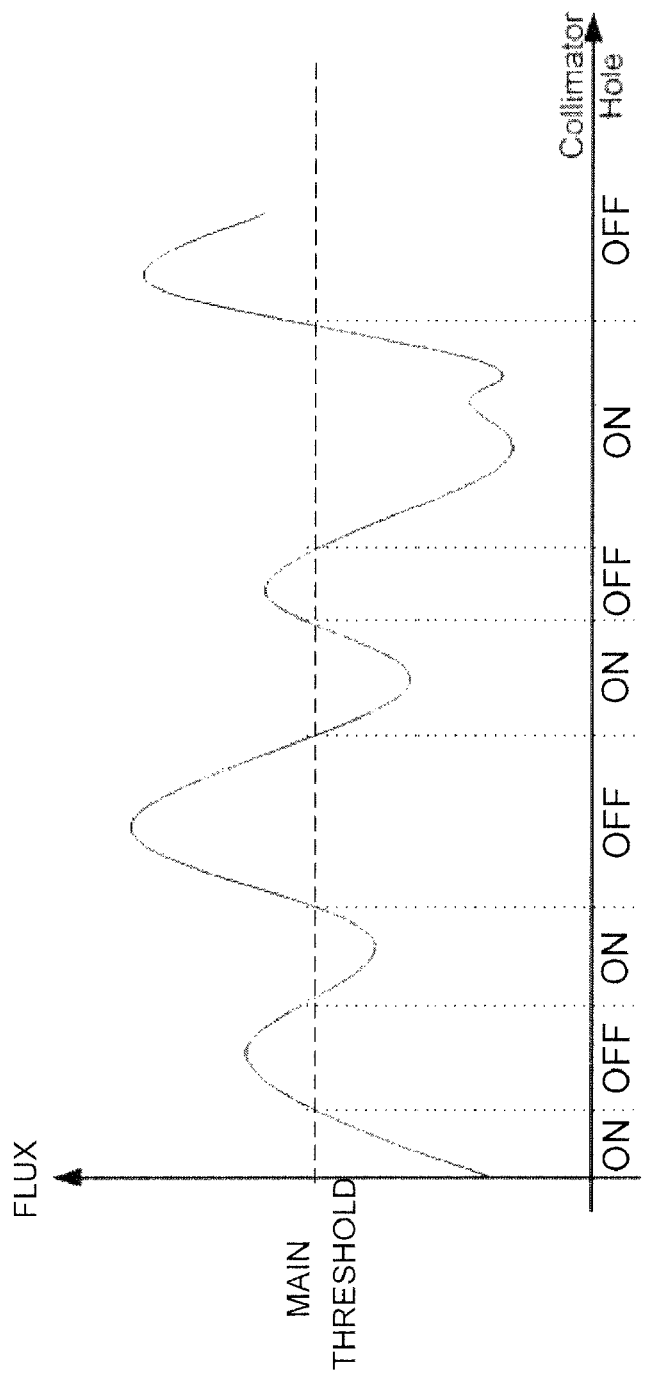
FIG. 10 is a plot illustrating a manner of equalization filtration of one embodiment of the present invention.

FIG. 10 is a plot illustrating a manner of equalization filtration of one embodiment of the present invention. In this embodiment, equalization filtration can be implemented by performing the first scan across the entire field of view or part of the field of view. A "main threshold" can be determined to limit exposure in each partial image of each rescan. Once desired exposure level or threshold has been achieved, the x-ray beam in partial images can be turned off or the x-ray beams associated with particular collimator holes can be turned off. With proper threshold value, partial images or collimator holes receiving exposure above the threshold will be turned off. In this manner, the dynamic range of exposure values can be compressed and dose can be saved. Image quality can be improved by reducing exposure in the light areas thus reducing the dynamic range.

In FIG. 10, the x-axis, labeled "Collimator Hole" represents the position of the scanning beam over subsequent apertures in collimation grid 90; it could also be viewed as a temporal axis, where the units of time are equal to the dwell time for a single aperture. The y-axis indicates the amount of x-ray flux emitted from an aperture that reaches detector 110 after penetrating some amount of patient volume. It can be seen that aperture 140 will be scanned by beam 40 or otherwise illuminated, i.e. "on," until the amount of x-ray flux from a given aperture reaching detector 110 exceeds the main threshold, at which point the electron beam is switched "off." If the flux drops below the main threshold, the electron beam is switched on again, and so forth.

Under an alternative embodiment of the present invention, equalization filtration can be done by calculating the rescan map in real time while the image is acquired. Implementation of the rescan map allows the imaging system to perform an equalization filtration scan in hardware, turning on or off the x-ray beam depending on how many rescans are needed. A complication is that there may be a hardware limit related to the grid control on the electron beam that limits the number of times that the x-ray beam can be turned on or off (number of switches) during each image acquisition frame. Such a limitation results from impedance, resistance, capacitance and inductance characteristics of the hardware. To limit the number of switches, equalization filtration can be modified by not only relying on a single threshold but rather considering a band of target counts, effectively low-pass filtering the rescan map. With a single threshold as in FIG. 10, the imaging system may switch 774 times or more. With a threshold band of target counts, the imaging system could reduce the number of switches to 548 or some other number below 774 or the number of switches experienced with a single threshold. With adjustment of threshold settings in the threshold band, the imaging system could further reduce the number of switches to 463 or some other number below 774 or the number of switches experienced with a single threshold.

The imaging system can implement equalization filtration using a threshold band, comprised of an upper maximum threshold and a lower minimum threshold, of target counts by saving or tracking exposure (flux) for each area or collimator hole in the rescan map. As the imaging system performs a scan, when the exposure or flux for an area or collimator hole increases from a level below a maximum threshold to a level just above the maximum threshold, the x-ray beam for the area or collimator hole is turned off. When the exposure or flux for an area or collimator hole falls below the maximum threshold, the x-ray beam for the area or collimator hole remains off. When the exposure or flux for an area or collimator hole decreases further to a level below a minimum threshold, the x-ray beam for the area or collimator hole is turned on. When the exposure or flux for an area or collimator hole increases above the minimum threshold, the x-ray beam for the area or collimator hole remains on. When the exposure or flux for an area or collimator hole increases above the maximum threshold, the x-ray beam for the area or collimator hole will be turned off. At different angles, the imaging system can save between 33% and 60% dose with an average dose saving of 47% using equalization filtration. Alternatively, dose saving of 41%, 43% or 45% of primary photons can be achieved.

If visualized using FIG. 10, the threshold band may appear as a horizontal line positioned higher on the y-axis than the main threshold representing the maximum threshold and a horizontal line positioned lower than the main threshold representing the minimum threshold. The state of the collimator hole would only switch from "on" to "off" when the flux transitioned from below to above the maximum threshold and would only switch from "off" to "on" when the flux transitioned from above to below the minimum threshold.

Under an alternative embodiment of the present invention, equalization filtration can be done by calculating the rescan map from a single frame of a real-time video and use it for the subsequent frame. Implementation of the rescan map in this manner allows the imaging system to perform an equalization filtration scan in hardware, thus turning on or off the x-ray beam depending on how many rescans are needed. This embodiment can be used with a single threshold or a threshold band.

Under an alternative embodiment of the present invention, the imaging system can utilize region of interest filtration, and two or more regions of interest can be selected. The first region of interest may maintain full image quality, with 8 rescans or the maximum number of rescans, and the second region of interest may only be imaged at significantly reduced image quality, with 1 or 2 rescans or a lower number of rescans than full image quality. Outside the second region of interest, the beam may turned off entirely via electronic collimation or another method. The rescan images can be aggregated based on the selection by the user or based on automatic or predetermined selection by the imaging system. The resulting detector images can be reconstructed and can be evaluated for image quality and dose savings. The user can toggle between region of interest filtration and standard acquisition mode on a frame by frame basis. Collimation can be but does not have to be toggled as well.

Region or regions of interest can be selected by the user or selected by the imaging system based on automatic or predetermined selection. After selection, the imaging system can define and implement region or regions of interest by deploying a mechanical shield or shutter to block electron beam 40 before x-ray target 50 or the x-ray beam after x-ray target 50. Shield or shutter can be made from tungsten, tungsten copper, tungsten alloy, lead, lead antimony, lead alloy, tantalum, tantalum alloy or other material with a high atomic number. (Materials with a high atomic number may successfully shield x-rays more so than materials with low atomic numbers.)

Under an alternative embodiment of the present invention, region or regions of interest can be selected by the user or selected by the imaging system based on automatic or predetermined selection from a variety of shapes including without limitation, circle, oval, ellipse, square, rectangle, triangle, polygon and quadrilateral shapes. The region or regions of interest can also be the entire field of view except the regions within the shape selected or the regions excluded by the shape. The size of the region or regions of interest can be any size or range of sizes up to the size of the field of view. In one embodiment of the present invention, the region of interest is set to the size of a human heart or one chamber of the human heart and is intended to expose only the heart or selected chamber to radiation. In another embodiment of the present invention, the region of interest is the size of human ovaries and is intended to exclude radiation from the ovaries.

To implement region of interest filtering, the imaging system can perform an initial scan across the entire field of view. Alternatively, the imaging system can utilize a previous saved scan or image. The imaging system can also perform one or more rescans across the entire field of view. The imaging system can then perform one or more rescans based on the shape selected or shape excluded at the size of the region of the interest. The rescan would only involve exposure for some area or collimator holes corresponding to the shape selected at the size of the region of interest. The rescan may involve all of the collimator holes within the shape selected or a portion of those collimator holes but would not involve areas or collimator holes outside the shape selected. In the example of a shape excluded, the rescan would only involve exposure for the area or collimator holes outside the shape excluded at the size of the region of interest. The imaging system can also perform one or more rescans based on one or more additional shapes selected or shapes excluded at one or more sizes of the region of the interest.

Under one embodiment of the present invention, the imaging system performs one initial scan and one rescan across the entire field of view, two rescans or one additional rescan across a rectangular region of interest corresponding to half of a human heart, and eight rescans or six additional rescans across a smaller region of interest within the rectangular region of interest. The entire field of view receives one initial scan and one rescan. The rectangular region of interest receives one initial scan and two rescans and the smaller region of interest within the rectangular region of interest receives one initial scan and eight rescans. Dose savings of up to 82% of the primary photons can be achieved utilizing this region of interest approach.

Under an alternative embodiment of the present invention, the specific region of interest can vary in position in the field of view over time. The region of interest can be a selected shape (e.g. circle, oval or ellipse) of a specified size that follows a contrast agent as it flows through vessels in the heart. The region of interest can be automatically selected by, for example, following the tip of a catheter or by following the bolus of a contrast medium. The region of interest can follow the edge of the contrast agent as it moves through vessels in the heart. The region of interest can also be time-based in a manner which tracks the motion of an organ such as the heart. The region of interest can be the area of the field of view experiencing motion.

Alternatively, the region of interest can be calculated by the imaging system. In a tomographic or tomosynthetic application, the user can select a single plane or multiple planes of interest. The user can select the region or regions of interest in the selected plane or planes; the region of interest can be selected by the user in three dimensions. The imaging system can then track the region of interest or regions of interest in following frames by incorporating motion within the field of view and calculating the relative position of the region of interest or regions of interest. Under an alternative embodiment of the present invention, equalization filtration can be combined with regions of interest to achieve maximal dose savings without detracting from the high image quality desired.

If target 50 includes a tungsten film, x-ray may be emitted through two mechanisms: Bremsstrahlung radiation, a direct results of the sudden deceleration of electrons by collision with heavier target particles, and K-line radiation, a result of incident electrons knocking target electrons out of their atomic "K" shell and other target electrons shedding energy to fill these created vacancies. Bremsstrahlung radiation takes on a spectrum of wavelengths and is the primary mechanism by which x-rays are emitted whereas K-line radiation emits a specific wavelength characteristic to the atomic structure of tungsten or target material and is the less prevalent mechanism.

Under an alternative embodiment of the present invention, the beam hardening filter is brought into close proximity of the tungsten film in x-ray target 50 and emitted K-line radiation can have a similar spatial extent as the primary (Bremsstrahlung) radiation and can be useful for imaging. X-ray target 50 can also have an additional film with a rare earth that has K-lines particularly well suited for imaging. Specifically, the rare earth can provide large contrast in iodine, a contrast medium used in interventional cardiology. Various rare earths can be used (e.g. Er, Gd, Dy, Sm) with different thicknesses (10 μm to 150 μm) and X-ray tube potentials (60 kVp to 90 kVp). A 150 μm layer of erbium in x-ray target 50 at 80 kVp can result in a low dose. The dose can be 87% of that found with 1 mm iodine using 0.1 mm Copper beam hardening filter, 70 kVp X-ray tube potential and maximum electron beam current of 210 mA. A reduced Er layer thickness of 120 μm can also be used and Er can be used in x-ray target 50. For the beam hardening filter the dose can be 96% with 1 mm iodine using 0.1 mm Copper beam hardening filter, 70 kVp X-ray tube potential and maximum electron beam current of 210 mA and for the integrated case it can 89%. Thus, using Er in the target can save 7.5% of the dose compared to using it as a beam hardening filter.

From a dose standpoint, a 150 μm Erbium target can be utilized. Er can be a significant thermal resistor that slowed the time to equilibrium temperatures significantly. A more convenient measure of time to equilibrium is the time to maximum temperature in the Be layer. With 1 mm iodine using 0.1 mm Copper beam hardening filter, 70 kVp X-ray tube potential and maximum electron beam current of 210 mA, this time can be 25 μs and for a 20 μm layer of Er the time can almost double. At the target thickness of 150 μm, the time can increase to 520 μs. Long times to equilibrate can lead eventually to overheating of x-ray target 50.

Real-time computing problems often require multiple graphics processing units (GPUs) to provide sufficient computing power to perform calculations in an allowable time budget. Incoming data is often streamed to these GPU devices at a continuous rate leading to severe performance losses on the GPU. These performance losses result from the fact that a single GPU must split resources between the aggregation/pre-processing of the data set and the subsequent computational processing of that complete data set. To overcome this problem, one GPU 1104 can be used as pre-processing engine, and a set of 1 to N (with N being a number between 1 and 100) GPUs as computational processing engines, e.g. reconstruction GPU 1105. The pre-processing engine captures the continuous data stream and aggregates it appropriately. This aggregated and pre-processed data is then distributed as a complete package to the processing GPUs using a single burst memory operation. Rather than receiving the data as a continuous stream, these processing GPUs receive a data package in short time interval only briefly interrupting its internal computational work. This allows the processing GPUs to almost perform at 100% of their rated performance by fully occupying the available computational resources for a longer time period.

Figure 11:
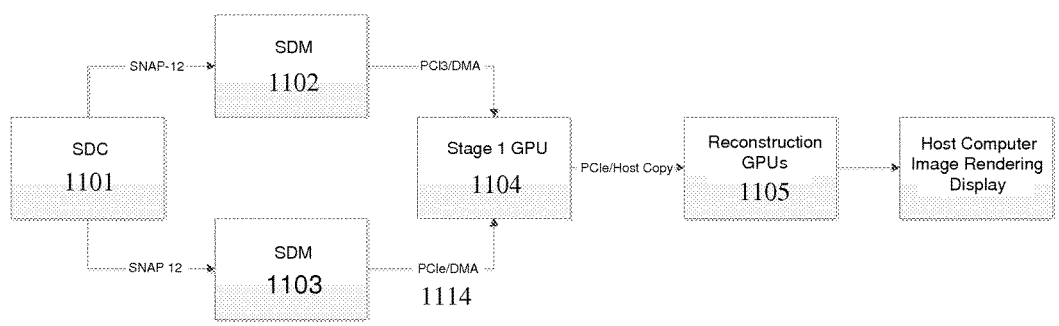
FIG. 11 is a diagram showing an overall architecture of one embodiment of the present invention.

FIG. 11 is a diagram showing an overall architecture of one embodiment of the present invention. Stage I GPU 1104 accumulates and pre-processes data directly from multiple SDM sources, then copies over the complete set via PCI-E bus 1115 to Stage II image reconstruction GPU(s) 1105 for the computational work. In one embodiment, pre-processing GPU 1104 can be a professional GPU with remote direct memory access (RDMA1) capability and the set of processing engines 1105 can be consumer grade GPUs without RDMA. In this case, the memory transfer between pre-processing GPU 1104 and processing GPUs 1105 is orchestrated by the host CPU. In another embodiment, all GPUs are professional-grade GPUs enabling memory transfers without host involvement. This has the advantage that the process is independent of the timing imposed by the operating system.

In one embodiment of the present invention, an array of GPUs to reconstruct data from an X-ray detector coming at a rate of 1 MHz. Each detector image contains of 160×80 bytes. Pre-processing GPU 1104 receives the detector data via RDMA1 and aggregates the detector data to frames of 100×100×160×80 bytes for 10 inch×10 inch array of apertures 140. This complete frame data is send to the processing GPUs 1105 at a rate of up to 30 Hz.

In one embodiment of the present invention, the architecture is used in a low-dose fluoroscopic system that has a large field of view (FOV), as required for use in interventional radiology. The system is expected to reduce entrance X-ray exposure and the radiation dose to the patient by a factor of 4 and the occupational dose by at least a factor of 2 at equal image quality as compared to a conventional system. The system is based on the Scanning-Beam Digital X-ray (SBDX) fluoroscope, a cardiac fluoroscopy system. Conventional fluoroscopy systems use an X-ray tube with a single focal spot and an extended detector, with the patient positioned close to the detector. In contrast, the imaging system can utilize an extended X-ray source that produces multiple focal spots. The radiation is focused from every focal spot position onto a pixelated detector with a custom collimator. The patient is positioned relatively far from the detector. Importantly, the final image is not generated from a single detector image as in conventional systems. Rather, it is comprised of up to 9,000 or 10,000 detector images that are reconstructed in real time. The largest gain in FOV is possible by employing two laterally spaced detectors compared to one detector in the SBDX cardiology system. A collimator can be used to illuminate both detectors by alternating the illumination pattern on a row by row basis.

In one embodiment of the present invention, one imaging frame every 130 ms can be produced. An imaging frame comprises 100×100 detector images of 160×80 detector pixels. The data are received by stage I GPU 1104 continuously and stored in an llh data buffer or accumulation data buffer that is transferred to stage II GPU 1105 once a frame is complete. The GPU reconstruction kernel uses as inputs the aggregated llh data buffer or accumulation data buffer, 2D detector data sets for each detector, the detector hole sum data, the current z focus value, and the amount to offset each output data image in the final reconstructed output.

GPU 1105 organizes its computation in blocks of worker threads, each of which can perform its own independent calculations and memory operations. These threads can operate on four basic types of memory; global, shared, texture, and local (register). The fastest memory is kept in thread local registers, and is a very limited resource only visible by the current working thread. Texture memory is read-only for the life of the workload, and can be accessed by all threads in all blocks with very little latency. Unfortunately this texture memory is limited and the slightly slower shared memory is only available to all the threads in a distinct thread block. Because most of the input data resides in the slowest global memory, a strategy to read/write from this space in non-random patterns must be implemented in order to complete the process in time. One such strategy is to load values in a vectorized fashion, which means a larger chunk of contiguous global memory is loaded, then broken down into subsets in thread local register memory.

The current llh input data buffer or accumulation data buffer can be stored in a format which splits the rows of data, mapping the right detector data to all odd rows, and the left detector data to all even rows. Each thread block uses this odd/even information to determine where in the output buffer the weighted values are to be added. Each thread in the GPU reconstruction kernel loads its required data in coalesced vectorized 4-element sections from global memory. Values which will be re-used by all threads in a particular block are stored locally in shared memory. The input values which are specific only to the current working thread will be loaded from global memory by the efficient vectorized method and stored in local register memory. Performance can be increased by allowing the kernel to load 16 llh frame values or accumulation frame values in a single operation by casting the load as the 16 byte unit 4 type. Each worker thread in a block loads a total of 32 values from the llh buffer or accumulation buffer by executing 2 contiguous 16 bytes loads. When writing to the output buffer, the reconstruction kernel makes use of the improved performance of the atomic operations on global memory. During this process each thread performs as many as 256 writes to global memory via the atomicAdd( ) operation. This method prevents a 'race' condition which arises when more than one working thread attempts to update the same memory location at the same time.

Once the reconstruction has been completed by the stage II GPU, the alpha-correction process is initiated with the intention of filtering the reconstructed image. This step performs a 2D separable box filter convolution and a 2D separable comb filter convolution on the reconstructed data. The result is an image which has these periodic artifacts removed, which greatly improves the image quality. This setup makes use of the RDMA1 capabilities of a professional grade GPU such as the Nvidia Tesla K20c, and the faster processing capabilities of a high-end consumer grade GPU such as the Nvidia Titan Black.

In one embodiment of the present invention, a 160×80 configuration is used for multi-detector array 110 and 100× 100 array of apertures 140 used for collimation grid 90. An imaging frame can comprise 100×100 detector images of 160×80 detector pixels. Each aperture 140 can act as a separate illumination point or source. Alternatively, the illumination points or sources can be infrared, ultrasound, microwave, visible light, electromagnetic, gamma ray, proton or other form of radiation. Each detector image of 160×80 detector pixels can be a separate image of the object. Since each aperture 140 is in a different position, the detector images of the object can be different for different apertures 140. The 100×100 array of apertures 140 can be formed as 100 columns of 100 rows or 100 rows of 100 columns. The imaging frame comprises of detector images from multiple illumination focal spot positions (in this example, 100×100) with 160×80 detector pixels. In this example, the illumination focal spot positions are in a single plane. In an alternative embodiment, the multiple illumination focal spot positions can be located around the object.

Each imaging frame can be formed after a single scan of the electron beam 40 over target 60 or 1307, dwelling on each targeted focal spot for a predetermined amount of time. Alternatively, the exposure time for each focal spot can be broken into multiple illuminations (rescans) separated in time. Use of multiple illuminations can keep the temperature of x-ray target 60 or 1307 below desired maximums (maximums being set by the potential of the target to "burn out" when overheated by the incident beam in a localized region). Thus, every focal-spot position can be rescanned 2 or more times and the imaging frame formed from 2 or more scans of the electron beam over each focal spot in target 60 or 1307.

A GPU with at least 3 Teraflops peak single-precision floating point performance can be used for GPU 1104. GPU 1104 can also act as a pre-processing, buffer constitution, buffer construction or data restructuring GPU operating as described herein. Memory bandwidth for board with ECC off can be at least 200 Gigabytes per second. The RDMA1 capability of GPU 1104 increases the data transfer rate from SDM 1102 and SDM 1103. A GPU with at least 4 Teraflops peak single-precision floating point performance can be used for processing or reconstruction GPU 1105. Memory bandwidth can be at least 336 Gigabytes per second.

As electron beam 40 scans each targeted focal spot for a predetermined amount of time, the imaging system stores a count of the number of incoming photons striking the detector surface of each detector of multi-detector array 110 in the data buffer. In the exemplary embodiment where the exposure time for each focal spot is broken into multiple illuminations (rescans) separated in time, GPU 1104 can sum or aggregate the photon counts for the illuminations or rescans over each targeted focal spot for each detector of multi-detector array 110. In this manner, an imaging frame can be developed with 100×100 detector images of 160×80 detector pixels. In an alternative embodiment, SDM 1102 and SDM 1103 or GPU 1104 can aggregate data from adjoining detector pixel elements and combine them into a single element with a lower bit value than the sum of 1-bit values of the adjoining detector pixels. In one example, four adjacent detector pixel elements with 1-bit values can be combined into a single element with a 3-bit value. With four adjacent detector pixel elements, the maximum value (when all four detector pixel elements are 1 or ON) is 4, a 3-bit value. With a 160×80 configuration for multi-detector array 110, a 160×80 element array with 1-bit values can be aggregate to an 80×40 element array with 3-bit values.

GPU 1104 can format and reshape the imaging frame and individual detector images of the 100×100 detector images. GPU 1104 can store data for each detector image of the 100×100 illumination focal spot positions comprising 160× 80 detector pixels into the proper address or location of the data buffer. GPU 1104 can also transpose the individual detector images. GPU 1104 can transform an imaging frame that is initially stored in row-by-row format (one row followed by another row, i.e. row major) into a column-by-column format (one column followed by another column, i.e. column major). GPU 1104 can also transform an imaging frame that is initially stored in column-by-column format (one column followed by another column, i.e. column major) into a row-by-row format (one row followed by another row, i.e. row major). GPU 1104 can also verify that there are no dropped holes representing dropped detector images for the set of 100×100 detector images. Dropped holes or dropped detector images can occur if GPU 1104 cannot process data quickly enough to keep up with SDM 1102 and SDM 1103. GPU 1104 checks for dropped holes or dropped detector images and reports it to the CPU. After completion of pre-processing of the imaging frame, the aggregated and pre-processed imaging frame data can be distributed from GPU 1104 as a complete package to processing or reconstruction GPU 1105 using a single burst memory operation.

Under an alternative embodiment, GPU 1104 is coupled to and receives data from two additional SDMs in addition to SDM 1102 and SDM 1103. Each pair of SDMs is coupled to and receives data from one scan data controller (SDC) 1101.

Under an alternative embodiment with 2 to N processing or reconstruction GPUs, GPU 1104 can split up the processing or reconstruction of an imaging frame of 100×100 detector images of 160×80 detector pixels into smaller imaging frames e.g. 10×10 detector images of 160×80 detector pixels or 100×2 detector images of 160×80 detector pixels. The number of detector images in the smaller imaging frame and the number of associated apertures 140 can be 2.5%, 5%, 10%, 20%, 25%, 33%, 40%, 50%, 60%, 70%, 75% or any percentage or range of percentages between 1% and 99% of the total number of detector images or associated apertures 140. Smaller imaging frames can allow more processing or reconstruction GPUs to operate concurrently or can allow the task to be split up more efficiently within a single GPU. Smaller imaging frames can also allow an individual reconstruction with involving that imaging frame to be accomplished faster. However, management of reconstruction process is less complex with larger imaging frames and associated smaller quantity of imaging frames. A range between 5% and 10%, 10% and 20% or 25% and 33% can be optimal.

The smaller imaging frames can comprise detector images for complete rows, e.g. 100×1, 100×2, 100×3, 100×4 or 100×5, or complete columns, e.g. 1×100, 2×100, 3×100, 4×100 or 5×100, of apertures 140. Imaging frames with complete rows or complete columns can be beneficial because it can parallel the scan motion of the scanning beam through array of apertures 140 reducing latency and possible conflict between detector data flow and processing or reconstruction by GPU 1105. The smaller imaging frame can comprise detector images for 1%, 2%, 3%, 4%, 5%, 7%, 10%, 15%, 20% or 25% of the total rows or columns or any number of rows or columns or any range between 2% and 25%. Smaller imaging frames can allow processing or reconstruction to commence with less waiting time for the scanning beam since the associated apertures 140 can be scanned faster with a smaller number. Smaller imaging frames can also allow an individual reconstruction with involving that imaging frame to be accomplished faster. However, management of reconstruction process is less complex with larger imaging frames and associated smaller quantity of imaging frames. A range between 2% and 5% of the total rows or columns, 5% and 10% of the total rows or columns or 10% and 20% of the total rows or columns can be optimal.

Each of the smaller imaging frames comprising a different subset or number of the total number of illumination focal spot positions can be transmitted to different processing or reconstruction GPUs for processing or reconstruction. The processing or reconstruction GPUs can perform reconstruction with the smaller imaging frame using a prior larger imaging frame e.g. 100×100 detector images of 160×80 detector pixels, in effect using the smaller imaging frame to update the prior larger imaging frame.

The foregoing descriptions of specific embodiments of the present invention have been presented for purposes of illustration and description. They are not intended to be exhaustive or to limit the invention to the precise forms disclosed, and many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. An x-ray imaging system for imaging an object comprising:
   a plurality of x-ray illumination source positions for producing x-ray radiation at each of said illumination source positions and projecting said x-ray radiation towards said object;
   a detector for detecting said x-ray radiation from said object and transmitting detector images for each of said illumination source positions;
   a memory buffer for storing said detector images from said detector;
   a first graphics processing unit coupled to said memory buffer for formatting said detector images and for constructing a complete frame data set with said detector images for each of said illumination source positions stored in said memory buffer;
   a second graphics processing unit coupled to said first graphics processing unit for receiving, from said first graphics processing unit, said complete frame data set with said detector images for each of said illumination source positions and for performing image reconstruction on said complete frame data set; and
   a bus coupled to said first graphics processing unit and said second graphics processing unit, wherein said complete frame data set with said detector images for each of said illumination source positions is transferred from said first graphics processing unit to said second graphics processing unit in a single burst operation.

2. The imaging system of claim 1 further comprising:
   a scanning beam x-ray source.

3. The imaging system of claim 1 further comprising:
   a direct memory access unit coupled to said first graphics processing unit for direct memory access of memory by said first graphics processing unit.

4. The imaging system of claim 1 further comprising:
   a direct memory access unit coupled to said first graphics processing unit for direct memory access of memory by said first graphics processing unit.

5. The imaging system of claim 1 further comprising:

a direct memory access unit coupled to said second graphics processing unit for direct memory access of memory by said second graphics processing unit.

6. The imaging system of claim 1 further comprising:
a PCI-E bus coupled to said first graphics processing unit and said second graphics processing unit.

7. The imaging system of claim 1 further comprising:
a third graphics processing unit coupled to said first graphics processing unit and said memory buffer for receiving said complete frame data set with said detector images for each of said illumination source positions and performing image reconstruction on said complete frame data set.

8. The imaging system of claim 1 wherein said second graphics processing unit further comprises a plurality of blocks of worker threads capable of performing independent calculations and memory operations.

9. The imaging system of claim 1 wherein said detector comprises a multi-detector array comprising a plurality of detector elements, wherein said memory buffer stores a count of incoming photons striking a surface of each of said detector elements, wherein exposures of each focal spot in said multi-detector array are separated in time, and wherein said first graphics processing unit sums said count for said exposures over said each focal spot for each of said detector elements.

10. The imaging system of claim 1 wherein said first graphics processing unit aggregates data from adjoining pixel elements of said detector and combines them as a single element.

11. The imaging system of claim 1 wherein said formatting said detector images comprises an operation selected from the group of: reshaping said detector images; transposing said detector images; transforming an image frame stored in a row-by-row format into a column-by-column format; and transforming an image frame stored in a column-by-column format into a row-by-row format.

12. A method for x-ray imaging of an object comprising:
producing x-ray radiation from a plurality of x-ray illumination source positions;
directing said x-ray radiation towards said object;
measuring an amount of said x-ray radiation striking a detector;
producing detector images of said object for each of said plurality of x-ray illumination source positions based on said amount of said x-ray radiation striking said detector;
using a first graphics processing unit to construct a complete frame data set with said detector images for each of said illumination source positions;
transmitting said complete frame data set with said detector images for each of said illumination source positions from said first graphics processing unit to a second graphics processing unit in a single burst operation; and
using said second graphics processing unit to perform image reconstruction on said complete frame data set received from said first graphics processing unit.

13. The method of claim 12 further comprising:
producing said complete frame data set at least once every 130 milliseconds.

14. The method of claim 12 further comprising:
identifying any of said detector images that are dropped from said complete frame data set using said first graphics processing unit.

15. The method of claim 12 further comprising:
aggregating image data for each of said illumination source positions to form said detector images.

16. The method of claim 12 further comprising:
transferring said complete frame data set with said detector images for each of said illumination source positions from said first graphics processing unit to said second graphics processing unit at a rate of 30 Hz.

17. The method of claim 12 further comprising:
organizing computation for said image reconstruction in blocks of worker threads wherein each of said worker threads performs independent calculations and memory operations.

18. The method of claim 12 further comprising:
aggregating image data for each of said illumination source positions to form said detector images; and
organizing computation for said image reconstruction in blocks of worker threads wherein each of said worker threads performs independent calculations and memory operations.

19. The method of claim 12 further comprising:
transmitting detector images from said detector at a rate of at least 1 MHz.

20. The method of claim 12 further comprising:
transposing said complete frame data set using said first graphics processing unit.

* * * * *